(12) United States Patent
Iacono et al.

(10) Patent No.: US 11,174,213 B2
(45) Date of Patent: Nov. 16, 2021

(54) EFFECTS OF CATALYST CONCENTRATION AND SOLID ACTIVATOR ON NICKEL-MEDIATED OLEFIN/CARBON DIOXIDE COUPLING TO ACRYLATES

(71) Applicant: CHEVRON PHILLIPS CHEMICAL COMPANY LP, The Woodlands, TX (US)

(72) Inventors: Pasquale Iacono, Bartlesville, OK (US); Mark L. Hlavinka, Tulsa, OK (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 16/159,381

(22) Filed: Oct. 12, 2018

(65) Prior Publication Data
US 2020/0115309 A1      Apr. 16, 2020

(51) Int. Cl.
*C07C 51/15*      (2006.01)
*B01J 21/04*      (2006.01)
(Continued)

(52) U.S. Cl.
CPC .............. *C07C 51/15* (2013.01); *B01J 21/04* (2013.01); *B01J 21/12* (2013.01); *B01J 27/055* (2013.01);
(Continued)

(58) Field of Classification Search
None
See application file for complete search history.

(56) References Cited

U.S. PATENT DOCUMENTS

| 3,390,128 A | 6/1968 | Hughes et al. |
| 3,623,973 A | 11/1971 | Tarhan |

(Continued)

FOREIGN PATENT DOCUMENTS

| CA | 2791834 | 9/2011 |
| CN | 103785469 | 5/2014 |

(Continued)

OTHER PUBLICATIONS

Mark Bishop, "Atoms First Version of An Introduction to Chemistry", 2019, Chiral Publishing Company, Chapter 1.5: Chapter 1—An Introduction to Chemistry (preparatorychemistry.com) (Year: 2019).*

(Continued)

*Primary Examiner* — Sudhakar Katakam
*Assistant Examiner* — Jennifer C Sawyer
(74) *Attorney, Agent, or Firm* — Eversheds Sutherland (US) LLP

(57) ABSTRACT

This disclosure provides for routes of synthesis of acrylic acid and other α,β-unsaturated carboxylic acids and their salts, including catalytic methods. For example, there is provided a process for producing an α,β-unsaturated carboxylic acid or a salt thereof, the process comprising: (1) contacting in any order, a group 8-11 transition metal precursor, an olefin, carbon dioxide, a diluent, and a metal-treated chemically-modified solid oxide such as a sulfur oxoacid anion-modified solid oxide, a phosphorus oxoacid anion-modified solid oxide, or a halide ion-modified solid oxide, to provide a reaction mixture; and (2) applying reaction conditions to the reaction mixture suitable to produce the α,β-unsaturated carboxylic acid or the salt thereof. Methods of regenerating the metal-treated chemically-modified solid oxide are described.

31 Claims, 1 Drawing Sheet

(51) Int. Cl.
*B01J 21/12* (2006.01)
*B01J 27/055* (2006.01)
*B01J 27/18* (2006.01)
*B01J 31/22* (2006.01)
*B01J 31/26* (2006.01)
*C07C 57/04* (2006.01)

(52) U.S. Cl.
CPC ....... *B01J 27/1806* (2013.01); *B01J 31/2208* (2013.01); *B01J 31/26* (2013.01); *C07C 57/04* (2013.01); *B01J 2523/17* (2013.01); *B01J 2523/18* (2013.01); *B01J 2523/19* (2013.01); *B01J 2523/67* (2013.01); *B01J 2523/68* (2013.01); *B01J 2523/69* (2013.01); *B01J 2523/821* (2013.01); *B01J 2523/822* (2013.01); *B01J 2523/824* (2013.01); *B01J 2523/827* (2013.01); *B01J 2523/828* (2013.01); *B01J 2523/842* (2013.01); *B01J 2523/845* (2013.01); *B01J 2523/847* (2013.01)

(56) References Cited

U.S. PATENT DOCUMENTS

| | | |
|---|---|---|
| 4,060,480 A | 11/1977 | Reed et al. |
| 4,452,910 A | 6/1984 | Hopkins et al. |
| 4,792,620 A | 12/1988 | Paulik et al. |
| 5,376,611 A | 12/1994 | Shveima |
| 6,107,230 A | 8/2000 | McDaniel et al. |
| 6,165,929 A | 12/2000 | McDaniel et al. |
| 6,294,494 B1 | 9/2001 | McDaniel et al. |
| 6,300,271 B1 | 10/2001 | McDaniel et al. |
| 6,316,553 B1 | 11/2001 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,524,987 B1 | 2/2003 | Collins et al. |
| 6,548,441 B1 | 4/2003 | McDaniel et al. |
| 6,548,442 B1 | 4/2003 | McDaniel et al. |
| 6,576,583 B1 | 6/2003 | McDaniel et al. |
| 6,613,712 B1 | 9/2003 | McDaniel et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,831,141 B2 | 12/2004 | McDaniel et al. |
| 6,936,667 B2 | 8/2005 | Jensen et al. |
| 6,992,032 B2 | 1/2006 | McDaniel et al. |
| 7,026,494 B1 | 4/2006 | Yang et al. |
| 7,041,617 B2 | 5/2006 | Jensen et al. |
| 7,148,298 B2 | 12/2006 | Jensen et al. |
| 7,199,073 B2 | 4/2007 | Martin et al. |
| 7,226,886 B2 | 6/2007 | Jayaratne et al. |
| 7,250,510 B2 | 7/2007 | Organ et al. |
| 7,294,599 B2 | 11/2007 | Jensen et al. |
| 7,312,283 B2 | 12/2007 | Martin et al. |
| 7,470,758 B2 | 12/2008 | Jensen et al. |
| 7,501,372 B2 | 3/2009 | Thorn et al. |
| 7,517,939 B2 | 4/2009 | Yang et al. |
| 7,576,163 B2 | 8/2009 | Yang et al. |
| 7,601,665 B2 | 10/2009 | McDaniel et al. |
| 7,619,047 B2 | 11/2009 | Yang et al. |
| 7,629,284 B2 | 12/2009 | Jensen et al. |
| 7,884,163 B2 | 2/2011 | McDaniel et al. |
| 8,309,485 B2 | 11/2012 | Yang et al. |
| 8,592,632 B2 | 11/2013 | Dahmen et al. |
| 8,623,973 B1 | 1/2014 | McDaniel et al. |
| 8,642,803 B2 | 2/2014 | Limbach et al. |
| 8,697,909 B2 | 4/2014 | Limbach et al. |
| 8,703,886 B1 | 4/2014 | Yang et al. |
| 8,940,940 B2 | 1/2015 | Dehn et al. |
| 9,023,959 B2 | 5/2015 | McDaniel et al. |
| 9,416,087 B2 | 8/2016 | Hlavinka et al. |
| 9,725,393 B2 | 8/2017 | Hlavinka et al. |
| 9,758,461 B2 | 9/2017 | Limbach et al. |
| 9,783,478 B2 | 10/2017 | Hlavinka et al. |
| 9,896,405 B2 | 2/2018 | Hlavinka et al. |
| 10,011,551 B2 | 7/2018 | Limbach et al. |
| 10,138,196 B2 | 11/2018 | Schaub et al. |
| 10,155,711 B2 | 12/2018 | Hlavinka et al. |
| 10,155,712 B2 | 12/2018 | Hlavinka et al. |
| 2010/0076167 A1 | 3/2010 | McDaniel et al. |
| 2011/0218359 A1 | 9/2011 | Limbach et al. |
| 2013/0172616 A1 | 7/2013 | Limbach et al. |
| 2015/0343431 A1 | 12/2015 | Parvulescu et al. |
| 2015/0344394 A1 | 12/2015 | Parvulescu et al. |
| 2016/0102039 A1 | 4/2016 | Hlavinka et al. |
| 2016/0130208 A1 | 5/2016 | Schaffner et al. |
| 2016/0229782 A1 | 8/2016 | Hlavinka et al. |
| 2016/0311745 A1 | 10/2016 | Hlavinka et al. |
| 2017/0166506 A1 | 6/2017 | Iacono et al. |
| 2017/0217869 A1 | 8/2017 | Limbach et al. |
| 2017/0283356 A1 | 10/2017 | Hlavinka et al. |
| 2017/0349523 A1 | 12/2017 | Hlavinka et al. |
| 2018/0127346 A1 | 5/2018 | Hlavinka et al. |
| 2018/0362434 A1 | 12/2018 | Iacono et al. |
| 2018/0362435 A1 | 12/2018 | Iacono et al. |
| 2018/0362436 A1 | 12/2018 | Hlavinka et al. |
| 2019/0062250 A1 | 2/2019 | Hlavinka et al. |
| 2019/0071381 A1 | 3/2019 | Iacono et al. |

FOREIGN PATENT DOCUMENTS

| | | |
|---|---|---|
| CN | 103785470 | 5/2014 |
| CN | 104418719 | 3/2015 |
| CN | 104418736 | 3/2015 |
| CN | 104418737 | 3/2015 |
| CN | 105622383 | 6/2016 |
| CN | 105622400 | 6/2016 |
| DE | 112014001125 | 11/2015 |
| EP | 2797869 | 8/2018 |
| EP | 3142992 | 9/2018 |
| IN | 201207472 | 12/2013 |
| IN | 201404656 | 9/2015 |
| WO | 2011/107559 | 9/2011 |
| WO | 2013/098772 | 7/2013 |
| WO | 2013/186238 | 12/2013 |
| WO | 2014/003195 | 1/2014 |
| WO | 2014/130410 | 8/2014 |
| WO | 2014/198469 | 12/2014 |
| WO | 2015/018793 | 2/2015 |
| WO | 2015/132031 | 9/2015 |
| WO | 2015/173276 | 11/2015 |
| WO | 2015/173277 | 11/2015 |
| WO | 2015/173295 | 11/2015 |
| WO | 2015/173296 | 11/2015 |
| WO | 2015/173307 | 11/2015 |
| WO | 2015/197699 | 12/2015 |
| WO | 2016/057449 | 4/2016 |
| WO | 2016/180775 | 11/2016 |
| WO | 2017/106176 | 6/2017 |
| WO | 2017/178282 | 10/2017 |

OTHER PUBLICATIONS

Mark Bishop, "Atoms First Version of An Introduction to Chemistry", 2019, Chiral Publishing Company, Chapter 2.2: Chapter 2—An Introduction to Chemistry: Unit Conversions (preparatorychemistry.com) (Year: 2019).*
Bernskoetter, Chem. Eur. J. 2014, 20, 3205-3211.
Bernskoetter, Organometallics, 2013, 32 (7), pp. 2152-2159.
Cavallo, L. Organometallics 2017, 36, 1107-1112.
Al-Ghamdi, et al., "Activity Relationship to Screen Ni-Bisphosphine Complexes for the Oxidative Coupling of CO2 and Ethylene," Organometallics, 2017, vol. 36, pp. 1107-1112.
Brand, et al., "Acid-Base Characterization of Aluminum Oxide Surfaces with XPS" J. Phys. Chem. B. 2004, 108, p. 6017-6024.
Bruckmeier et al., "Formation of Methyl Acrylate from CO2 and Ethylene via Methylation of Nickelalactones", Organometallics, 2010, vol. 29, pp. 2199-2202.

(56) References Cited

OTHER PUBLICATIONS

Deutschmann, "Heterogeneous Catalysis and Solid Catalysts, 2. Development and Types of Solid Catalysts," Ullmann's Encyclopedia of Industrial Chemistry, published online Oct. 15, 2011, pp. 483-549, doi: 10.1002/14356007. o05_o02.
Eigenberger, "Catalytic Fixed-Bed Reactors," Ullmann's Encyclopedia of Industrial Chemistry, 2012, pp. 1-66, doi:10.1002/14356007. b04_199.pub2.
Fischer et al., "Zur Synthese und Charakterisierung van N, N'—Tetramethylethylendiamin-nickelacyclopropionat", Z. anorg. allg. Chem., 1989, vol. 577, pp. 111-114.
Fischer, et al.., "A key step in the formation of acrylic acid from CO2 and ethylene: the transformation of a Nickelalactone into a nickel-acrylate complex"; Chem. Commun., 2006, pp. 2510-2512.
Gordillo et al. "Catalytic route to acrylates from alkenes and CO2" Abstracts of Papers, 245th ACS National Meeting & Exposition, New Orleans, LA, United States, Apr. 7-11, 2013 (2013), INOR-1109. Language: English, Database: Caplus.
Hendricksen, "Catalytic Formation of Acrylate from Carbon Dioxide and Ethene," Chemistry, A European Journal, 2014, vol. 20, pp. 12037-12040.
Hoberg et al., "Nickel(O)-Induzierte C-C-Verknüpfung Zwischen Kohlendioxid und Ethylen Sowie Mono-Oder Di-Substituierten Alkenen"; Journal of Organometallic Chemistry, 1983, vol. 251, pp. C51-C53.
Huguet et al., "Nickel-Catalyzed Direct Carboxylation of Olefins with CO2: One-Pot Synthesis of a, β-Unsaturated Carboxylic Acid Salts", Chem. Eur. J., 2014, vol. 20, pp. 16858-16862.
Jin et al., "Effect of Sodium Cation on Metallacycle β-Hydride Elimination in CO2-Ethylene Coupling to Acrylates", Chem. Eur. J.,_2014, vol. 20, pp. 3205-3211.
Jin et al., "Lewis Acid Induced β-Elimination from a Nickelalactone: Efforts toward Acrylate Production from CO2 and Ethylene", Organometallics, 2013, vol. 32, pp. 2152-2159.
Knopf et al., "A family of cis-macrocyclic diphosphines: modular, stereoselective synthesis and application in Catalytic CO2/ethylene coupling", Chemical Science, 2017, vol. 8 (Issue 2), pp. 1463-1468. doi:10.1039/c6sc03614g.
Kraus, "Ni-Catalyzed Synthesis of Acrylic Acid Derivatives from CO2 and Ethylene," Topics in Organometallic Chemistry, vol. 53, 2015, p. 199-223.
Krillov et al., "Carboxylic acid derivatives via catalytic carboxylation of unsaturated hydrocarbons: whether the nature of a reductant may determine the mechanism of CO2 incorporation?", Dalton Trans., 2015, vol. 44, 16212-16223.
Langer et al., "A new set of nickelacyclic carboxylates ("nickelalactones") containing pyridine as supporting ligand: synthesis, structures and application in C-C- and C-S linkage reactions"; Journal of Organometallic Chemistry, 2004, vol. 689, pp. 2952-2962.
Lejkowski et al, "The First Catalytic Synthesis of an Acrylate from CO2 and an Alkene—A Rational Approach"; Chem. Eur. J., 2012, vol. 18, pp.
Limbach et al., "Investigation of fundamental steps in the formation of acrylates from CO2 and ethylene", Abstracts of Papers, 243rd ACS National Meeting & Exposition, San Diego, CA, United States, Mar. 25-29, 2012 (2012), NOR-1216. Language: English, Database: CAPLUS.
Limbach, "Acrylates from Alkenes and CO2, the Stuff That Dreams Are Made of," Advances in Organometallic Chemistry 2015, vol. 63, Chapter 4, pp. 175-202.
Limbach, et al., "CO2 as C1 building block for the synthesis of acrylates and beyond", From Abstracts of Papers, 247th ACS National Meeting & Exposition, Dallas, TX, United States, Mar. 16-20, 2014 (2014), CATL-116. Language: English, Database: Caplus.
Manzini et al., "Enhanced activity and recyclability of palladium complexes in the catalytic synthesis of sodium acrylate from CO2 and ethylene" ChemCatChem, 2016. doi:10.1002/cctc.201601150.
Manzini et al., "Palladium- and Nickel-Catalyzed Synthesis of Sodium Acrylate from Ethylene, CO2, and Phenolate Bases: Optimization of the Catalytic System for a Potential Process", Eur. J_ Org. Chem., 2015, pp. 7122-7130.
Manzini et al., "Synthesis of acrylates from olefins and CO2 using sodium alkoxides as bases", Catalysis Today, 2016, http://dx.doi.org/10_1016/j.cattod.2016.03.025.
Newkirk, "Drying and Decomposition of Sodium Carbonate," Analytical Chemistry, vol. 30, No. 5, 1958, pp. 982-984.
Norskov et al., Nature Chemistry, Towards the Computational Design of Solid Catalysts, 2009, 1, pp. 37-46.
Papai et al., "Mechanistic Details of Nickel(O)-Assisted Oxidative Coupling of CO2 with C2H4"; Organometallics, 25004, vol. 23, pp. 5252-5259.
Pinnavaia, T. J., "Intercalated Clay Catalysts," Science, 1983, vol. 220, No. 4595, pp. 365-371.
Plessow et al., "Acrylate Formation from CO2 and Ethylene Mediated by Nickel Complexes: A Theoretical Study", Oganometallics, 2014, vol. 33, pp. 3657-3668.
Plessow et al., "Mechanistic Details of the Nickel-Mediated Formation of Acrylates from CO2, Ethylene and Methyllodide", Organometallics, 2013, vol. 32, pp. 3327-3338.
Prasetyo, "Development of heterogenized catalyst systems for the synthesis of acrylic acid derivatives from carbon dioxide and ethylene," University of Stuttgart, Doctoral Thesis, Date of oral test: Apr. 20, 2015, 275 pages.
Stieber et al., "Acrylate formation from CO2 and ethylene: catalysis with palladium and mechanistic insight", Chem. Commun., 2015, vol. 51, pp. 10907-10909.
Thomas, J.M., "Sheet Silicate Intercalates: New Agents for Unusual Chemical Conversions*", Intercalation Chemistry, Academic Press, Inc., 1982, Ch. 3, pp. 55-99.
Wang, "Synthesis of Acrylic Acid Derivatives from CO2 and Ethylene," Chem, 3, 211-228, 2017.
Yu et al., "Carboxylation of olefins/alkynes with CO2 to industrially relevant acrylic acid derivatives", Journal of CO2 Utilization, 2013, vol. 1, pp. 60-68.
Kang, International Review of Chemical Engineering (I.RE.CH.E.), vol. 5, N. 2, p. 133.
Kosolapoff, J. Am. Chem. Soc. 1947, 69, 2020.
Krauss,Topics in Organometallic Chemistry, vol. 53, 2015, pp. 199-223.
Limbach, Chem. Eur. J. 2012, 18, 14017-14025.
Schaub, T. Eur. J. Org. Chem. 2015, 7122.
Walther, Chem. Commun., 2006,0, 2510-2512.
Walther, Journal of Organometallic Chemistry, 2004, 689, 2952-2962.
International Search Report and the Written Opinion of the International Searching Authority in PCT/US2019/55147 dated Jan. 15, 2020, 9 pages.
Melissa N. Hopkins, Kenichi Shimmei, Katherine B. Uttley, and Wesley H. Bernskoetter, Synthesis and Reactivity of 1,2-Bis(di-isopropylphosphino)benzene Nickel Complexes: A Study of Catalytic C02-Ethylene Coupling, Organometallics, Jul. 12, 2018, 37(20), pp. 3573-3580.

* cited by examiner

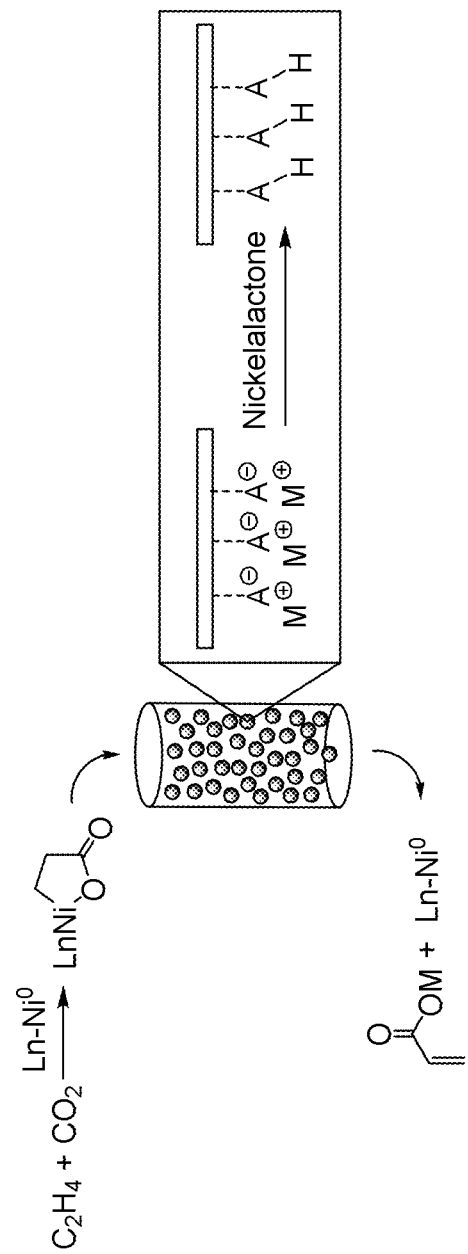

EFFECTS OF CATALYST CONCENTRATION AND SOLID ACTIVATOR ON NICKEL-MEDIATED OLEFIN/CARBON DIOXIDE COUPLING TO ACRYLATES

CROSS REFERENCE TO RELATED APPLICATIONS

None.

TECHNICAL FIELD

This disclosure relates to routes of synthesis of acrylic acid, other α,β-unsaturated carboxylic acids and salts thereof, including catalytic methods.

BACKGROUND

The majority of industrially synthesized chemical compounds are prepared from a limited set of precursors, whose ultimate sources are primarily fossil fuels. As these reserves diminish, it would be beneficial to use a renewable resource, such as carbon dioxide, which is a non-toxic, abundant, and economical $C_1$ synthetic unit. The coupling of carbon dioxide with other unsaturated molecules holds tremendous promise for the direct preparation of molecules currently prepared by traditional methods not involving $CO_2$.

One could envision the direct preparation of acrylates and carboxylic acids through this method, when carbon dioxide is coupled with olefins. Currently, acrylic acid is produced by a two-stage oxidation of propylene. The production of acrylic acid directly from carbon dioxide and ethylene would represent a significant improvement due to the greater availability of ethylene and carbon dioxide versus propylene, the use of a renewable material ($CO_2$) in the synthesis, and the replacement of the two-step oxygenation process currently being practiced.

Therefore, what is needed are improved methods for preparing acrylic acid and other α,β-unsaturated carboxylic acids, including catalytic methods.

SUMMARY

This summary is provided to introduce various concepts in a simplified form that are further described below in the detailed description. This summary is not intended to identify required or essential features of the claimed subject matter nor is the summary intended to limit the scope of the claimed subject matter.

In an aspect, this disclosure provides processes, including catalytic processes, for producing α,β-unsaturated carboxylic acids or salts thereof utilizing as an activator a metal-treated chemically-modified solid oxide, in which the chemically-modified solid oxide comprises or is selected from a solid oxide that is chemically modified with an electron-withdrawing anion, for example, a sulfur oxoacid anion-modified solid oxide, a phosphorus oxoacid anion-modified solid oxide, or a halide ion-modified solid oxide. In an aspect, for example, the solid oxide of the chemically-modified solid oxide can comprise or be selected from silica, alumina, titania, zirconia, magnesia, boria, calcia, zinc oxide, silica-alumina, silica-coated alumina, silica-titania, silica-zirconia, and other oxides. In another aspect, for example, the solid oxide can be chemically modified with sulfate, bisulfate, fluorosulfate, phosphate, fluorophosphate, fluoride, chloride, and other anions, including combinations thereof. The metal-treated aspect of this activator can be provided by treatment of the chemically-modified solid oxide with a source of a metal cation, for example, a metal cation comprising or selected from a Group 1, 2, 12 or 13 metal.

When a transition metal precursor compound is treated with an olefin such as ethylene and carbon dioxide ($CO_2$) in the presence of the metal-treated chemically-modified solid oxide activator in a reaction mixture that includes a diluent, under suitable reaction conditions, an α,β-unsaturated carboxylic acid or the salt thereof is formed in which the reaction can be catalytic. The transition metal precursor and any transition metal compound formed in the reaction may be referred to in this disclosure as a catalyst, even when the coupling reaction is not catalytic. In one aspect, it has been discovered that when a transition metal precursor compound (catalyst), such as a nickel compound, is present in the reaction mixture at concentrations of less than 0.2 mM (millimolar), the yield of the α,β-unsaturated carboxylic acid or a salt thereof can increase over the yield obtained in a 0.2 mM transition metal concentration mixture under otherwise the same reaction conditions.

Moreover, a sulfur oxoacid anion-modified solid oxide, a phosphorus oxoacid anion-modified solid oxide, or a halide ion-modified solid oxide, when metal-treated according to this disclosure, are effective at providing higher yields of the α,β-unsaturated carboxylic acid or the salt thereof with decreasing concentrations of the transition metal precursor compound. By developing the disclosed heterogeneous system, there is provided a distinct advantage in ease of separation of the desired product from the catalytic system.

According to an aspect of this disclosure, there is provided a process for forming an α,β-unsaturated carboxylic acid or a salt thereof, the process comprising:
 a) contacting in any order
  i) a transition metal precursor compound comprising at least one first ligand;
  ii) optionally, at least one second ligand;
  iii) an olefin;
  iv) carbon dioxide ($CO_2$);
  v) a diluent; and
  vi) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
 b) subjecting the reaction mixture to reaction conditions suitable to form the α,β-unsaturated carboxylic acid or the salt thereof.

In an aspect, the transition metal precursor compound (catalyst) can be present in the reaction mixture at a concentration of less than 0.2 mM (millimolar).

In another aspect, this disclosure provides a process for forming an α,β-unsaturated carboxylic acid or a salt thereof, the process comprising:
 a) contacting
  i) a metalalactone compound;
  ii) a diluent; and
  iii) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
 b) subjecting the reaction mixture to reaction conditions suitable to form the α,β-unsaturated carboxylic acid or the salt thereof.

In an aspect, the metalalactone can be present in the reaction mixture at a concentration of less than 0.2 mM (millimolar). According to an aspect, this reaction mixture can comprise an adduct of the metalalactone and the metal-treated chemically-modified solid oxide.

This summary and the following detailed description provide examples and are explanatory only of the invention. Accordingly, the foregoing summary and the following detailed description should not be considered to be restrictive. Additional features or variations thereof can be provided in addition to those set forth herein, such as for example, various feature combinations and sub-combinations of these described in the detailed description.

BRIEF DESCRIPTION OF THE DRAWING

The FIGURE illustrates one aspect of this disclosure, showing the use a metal-treated chemically-modified solid oxide (MT-CMSO) as a stationary phase activator in a column configuration, in which formation of the acrylate coupling reaction of ethylene and $CO_2$ to form a metalalactone such as a nickelalactone in a mobile phase can be effected, and the resulting nickelalactone can be destabilized by the metal-treated chemically-modified solid oxide stationary phase to form an acrylate product. The MT-CMSO and CMSO structures illustrated in the FIGURE are nominal or idealized structures, which are formalized to reflect general stoichiometries and are not intended to suggest actual structural features. Examples of chemically-modified solid oxide comprises a sulfur oxoacid anion-modified solid oxide, a phosphorus oxoacid anion-modified solid oxide, or a halide ion-modified solid oxide.

DEFINITIONS

To define more clearly the terms used herein, the following definitions are applicable to this disclosure unless otherwise indicated. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated by reference conflicts with the definition or usage provided herein, the definition or usage provided herein controls.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

While compositions and methods are described in terms of "comprising" various components or steps, the compositions and methods can also "consist essentially of" or "consist of" the various components or steps, unless stated otherwise.

The terms "a", "an", and "the" are intended to include plural alternatives, e.g., at least one. For instance, the disclosure of "a chemically-modified solid oxide", "a diluent", "a catalyst", and the like, is meant to encompass one, or mixtures or combinations of more than one chemically-modified solid oxide, diluent, catalyst, and the like, unless otherwise specified.

The terms "including", "with", and "having", as used herein, are defined as comprising (i.e., open language), unless specified otherwise.

The term "hydrocarbon" refers to a compound containing only carbon and hydrogen. Other identifiers can be utilized to indicate the presence of particular groups in the hydrocarbon, for instance, a halogenated hydrocarbon indicates the presence of one or more halogen atoms replacing an equivalent number of hydrogen atoms in the hydrocarbon.

As used herein, the term "α,β-unsaturated carboxylic acid" and its derivatives refer to a carboxylic acid having a carbon atom of a carbon-carbon double bond attached to the carbonyl carbon atom (the carbon atom bearing the double bonded oxygen atom). Optionally, the α,β-unsaturated carboxylic acid can contain other functional groups, heteroatoms, or combinations thereof.

As used herein, the term "sulfur oxoacid anion" in the context of suitable sulfur oxoacid anion sources that can be used to prepare the sulfur oxoacid anion-modified solid oxide, include both substituted including halide-substituted and non-substituted sulfur oxoacid anions. For example, the term "sulfur oxoacid anion" is intended to include but not be limited to, sulfate, bisulfate, fluorosulfate, alkyl sulfonate (for example, mesylate or methanesulfonate), aryl sulfonate (for example, tosylate or toluenesulfonate), fluoroalkyl sulfonate (for example, triflate or trifluoromethanesulfonate), fluoroaryl sulfonate (for example, for example, $[CF_3C_6H_4SO_3]^-$), and thiosulfate, and any combination thereof. For example, the alkyl sulfonate can be a $C_1$-$C_{10}$ alkyl sulfonate, the aryl sulfonate can be a $C_6$-$C_{14}$ aryl sulfonate, the fluoroalkyl sulfonate can be a $C_1$-$C_{10}$ fluoroalkyl sulfonate, and the fluoroaryl sulfonate can be a $C_6$-$C_{14}$ fluoroaryl sulfonate.

Also as used herein, the term "phosphorus oxoacid anion" in the context of suitable phosphorus oxoacid anion sources that can be used to prepare the phosphorus oxoacid anion-modified solid oxide, include both substituted including halide-substituted and non-substituted phosphorus oxoacid anions. For example, the term "phosphorus oxoacid anion" is intended to include but not be limited to, phosphate, monofluorophosphate, difluorophosphate, or similar anions, or any combination thereof. Unless specified otherwise, the term "fluorophosphate" or "fluorophosphates" include both monofluorophosphate ($[PO_3F]^{2-}$) and difluorophosphate ($[PO_2F_2]^-$).

For any particular compound or group disclosed herein, any name or structure presented is intended to encompass all conformational isomers, regioisomers, stereoisomers, and mixtures thereof that may arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to pentane includes n-pentane, 2-methyl-butane, and 2,2-dimethylpropane; and a general reference to a butyl group includes a n-butyl group, a sec-butyl group, an iso-butyl group, and a t-butyl group, unless indicated otherwise.

Various numerical ranges are disclosed herein. When Applicants disclose or claim a range of any type, Applicants' intent is to disclose or claim individually each possible number that such a range could reasonably encompass, including end points of the range as well as any sub-ranges and combinations of sub-ranges encompassed therein, unless otherwise specified. For example, by disclosing a temperature of from 70° C. to 80° C., Applicant's intent is to recite individually 70° C., 71° C., 72° C., 73° C., 74° C., 75° C., 76° C., 77° C., 78° C., 79° C., and 80° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if Applicants disclose in an aspect of the disclosure that one or more steps in the processes disclosed herein can be conducted at a temperature in a range from 10° C. to 75° C., this range should be interpreted as encompassing temperatures in a range from "about" 10° C. to "about" 75° C.

Values or ranges may be expressed herein as "about", from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about", it will be understood that the particular value forms another embodiment. It will be further understood that there are a number of values disclosed therein, and that each value is also herein disclosed as "about" that particular value in addition to the value itself. In another aspect, use of the term "about" means ±20% of the stated value, ±15% of the stated value, ±10% of the stated value, ±5% of the stated value, ±3% of the stated value, or ±1% of the stated value.

Applicants reserve the right to proviso out or exclude any individual members of any such group of values or ranges, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants can be unaware of at the time of the filing of the application.

The term "substituted" when used to describe a group, for example, when referring to a substituted analog of a particular group, is intended to describe the compound or group wherein any non-hydrogen moiety formally replaces hydrogen in that group or compound, and is intended to be non-limiting. A compound or group can also be referred to herein as "unsubstituted" or by equivalent terms such as "non-substituted", which refers to the original group or compound. "Substituted" is intended to be non-limiting and include inorganic substituents or organic substituents as specified and as understood by one of ordinary skill in the art.

The terms "contact product", "contacting", and the like, are used herein to describe compositions and methods wherein the components are contacted together in any order, in any manner, and for any length of time, unless specified otherwise. For example, the components can be contacted by blending or mixing. Further, unless otherwise specified, the contacting of any component can occur in the presence or absence of any other component of the compositions and methods described herein. Combining additional materials or components can be done by any suitable method. Further, the term "contact product" includes mixtures, blends, solutions, slurries, reaction products, and the like, or combinations thereof. Although "contact product" can, and often does, include reaction products, it is not required for the respective components to react with one another. Similarly, "contacting" two or more components can result in a reaction product or a reaction mixture. Consequently, depending upon the circumstances, a "contact product" can be a mixture, a reaction mixture, or a reaction product.

Although any methods and materials similar or equivalent to those described herein can be used in the practice or testing of the invention, the typical methods and materials are herein described.

The Abstract of this application is not intended to be used to construe the scope of the claims or to limit the scope of the subject matter that is disclosed herein, but rather to satisfy the requirements of 37 C.F.R. § 1.72(b), to enable the United States Patent and Trademark Office and the public generally to determine quickly from a cursory inspection the nature and gist of the technical disclosure. Moreover, any headings that are employed herein are also not intended to be used to construe the scope of the claims or to limit the scope of the subject matter that is disclosed herein. Any use of the past tense to describe any example otherwise indicated as constructive or prophetic is not intended to reflect that the constructive or prophetic example has actually been carried out.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

DETAILED DESCRIPTION

The present disclosure is directed generally to methods for forming α,β-unsaturated carboxylic acids, or salts thereof. An illustrative example of a suitable α,β-unsaturated carboxylic acid is acrylic acid.

According to one aspect, this disclosure provides for the formation of an α,β-unsaturated carboxylic acids and salts thereof from metalalactones and a solid activator comprising or selected from a metal-treated chemically-modified solid oxide (MT-CMSO) such as those solid oxide activators described here. One example of the α,β-unsaturated carboxylic acid salt formation from exemplary metalalactones and a MT-CMSO is illustrated in Scheme 1, which provides for a nickel catalytic coupling reaction between an olefin and $CO_2$ and formation of an acrylate. As explained herein, Scheme 1 is not limiting but is exemplary, and each reactant, catalyst, CMSO and MT-CMSO, and product are provided for illustrative purposes. Examples of chemically-modified solid oxide comprises a sulfur oxoacid anion-modified solid oxide, a phosphorus oxoacid anion-modified solid oxide, or a halide ion-modified solid oxide as further described herein.

Scheme 1

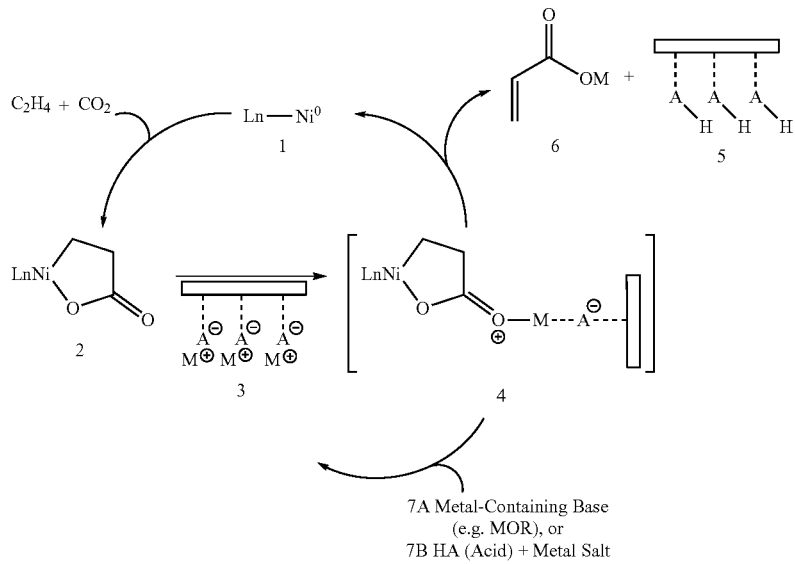

7A Metal-Containing Base
(e.g. MOR), or
7B HA (Acid) + Metal Salt

In Scheme 1, a transition metal catalyst as disclosed herein is illustrated generally by a nickel(0) catalyst at compound 1, and the olefin disclosed herein, generally an α-olefin, is illustrated by ethylene. In the presence of the catalyst 1, the olefin couples with $CO_2$ to form the metalalactone 2. Metalalactone 2 is destabilized by its interaction with a metal-treated chemically-modified solid oxide (MT-CMSO) such as a metal-treated sulfur oxoacid anion-modified solid oxide (including, for example, fluorosulfate-modified solid oxides), a metal-treated phosphorus oxoacid anion-modified solid oxide (including, for example, fluorophosphate-modified solid oxides), or a metal-treated halide ion-modified solid oxide, 3. While not intending to be bound by theory, the MT-CMSO solid activators comprise associated metal cations, which are thought to interact with metalalactone 2 in some fashion, for example to form an adduct of some type, such as one illustrated as intermediate 4. Reaction of the combined MT-CMSO solid activator 3 and metalalactone 2 (or intermediate of some type, represented generally as 4) proceeds to eliminate or release the metal acrylate 6, for example, from adduct 4, and regenerates catalyst compound 1 and byproduct solid oxide 5, which in an aspect can comprise a chemically-modified solid oxide (CMSO) comprising oxoacid moieties, but generally fewer cationic metal sites as the MT-CMSO. The CMSO can be regenerated to the MT-CMSO by either [1] treatment with a metal-containing base such as a metal hydroxide or metal alkoxide, or metal alkyl amide, 7A, or [2] treatment with an acid and a metal salt, for example, a combination of $H_2SO_4$ and NaCl, 7B. While not intending to be theory-bound, the resulting MT-CMSO is believed to have accessible metal sites that are capable of interacting with the metalalactone, for example, as illustrated in Scheme 1.

Scheme 1 is not intended to reflect a reaction mechanism, and the MT-CMSO and CMSO structures illustrated in Scheme 1 are nominal or idealized structures, which are not intended to reflect actual chemical structures. The participation of the solvent and/or other reaction components in the elimination or release of the metal acrylate 6, is not fully understood but may include direct participation in the reaction or simply solvating an acrylate salt which is generally insoluble in the diluent. Other routes of synthesis of acrylic acid, other α,β-unsaturated carboxylic acids and salts thereof are described in U.S. Pat. Nos. 9,416,087; 9,725,393; 9,783,478; and 9,896,405; each of which is incorporated by reference in its entirety.

In an aspect, this disclosure and the Examples demonstrate the effects of varying the initial metal catalyst concentrations and the co-catalyst (MT-CMSO) on the acrylate yield. Among other things, it is shown that while all the MT-CMSO activators tested have activity, the metal-treated (in this case, sodium treated) sulfated solid oxides show good catalytic performance based on acrylate yield (turnover). It is also shown that a decrease in the concentration of the transition metal catalyst from an initial concentration resulted in an increase in the turnover number, regardless of the source of the metal treatment of the CMSO. For example, $Ni(COD)_2$/bis(phosphine) loadings were varied using different sodium-treated or doped solid supports, and it was demonstrated that a decrease in concentration from 0.2 mM initial concentration increased the turnover number regardless of the sodium source employed. The sodium-treated sulfated-alumina showed the highest turnover numbers, although the sodium-treated fluorided silica-coated alumina showed good activity, which also increased as the initial nickel catalyst concentration decreased from its initial concentration from 0.2 mM.

Chemically-Modified Solid Oxide (CMSO) Activator (Co-Catalyst)

The chemically-modified solid oxides (CMSO) of the present disclosure have been described in, for example, U.S. Pat. Nos. 8,703,886, and 9,023,959, which are incorporated by reference herein in their entireties. The CMSO materials described here are used in the formation of the metal-treated CMSO materials that are useful in the acrylate production process of this disclosure.

In one aspect, this disclosure encompasses a process wherein the activator or co-catalyst can comprise a metal oxide. In an aspect, the activator can comprise a calcined metal oxide. Examples of metal oxides include, but are not limited to, silica, alumina, silica-alumina, silica-coated alumina, aluminum phosphate, aluminophosphate, heteropolytungstate, mullite, boehmite, titania, zirconia, magnesia, boria, zinc oxide, silica-titania, silica-zirconia, a mixed oxide thereof, or any mixture thereof.

The activator also can comprise, for example, a chemically-modified solid oxide, or CMSO (also termed a chemically-treated solid oxide). In an aspect, the activator can comprise, consist of, consist essentially or, or be selected from a chemically-modified solid oxide. The term "chemically-modified solid oxide" is used interchangeably with similar terms such as, "solid oxide treated with an electron-withdrawing anion", "treated solid oxide", and the like. While not intending to be bound by theory, it is thought that the chemically-modified solid oxide can serve as an acidic activator-support which allows it to function as the activator in the process disclosed herein.

In one aspect of this disclosure, the activator can comprise at least one chemically-modified solid oxide comprising at least one solid oxide treated with at least one electron-withdrawing anion, wherein the solid oxide can comprise any oxide that is characterized by a high surface area, and the electron-withdrawing anion can comprise any anion that increases the acidity of the solid oxide as compared to the solid oxide that is not treated with at least one electron-withdrawing anion.

In another aspect of this disclosure, the activator can comprise at least one chemically-modified solid oxide, comprising at least one solid oxide treated with at least one electron-withdrawing anion. For example, the solid oxide can comprise, consist of, consist essentially of, or can be selected from at least one of silica, alumina, silica-alumina, silica-coated alumina, aluminum phosphate, aluminophosphate, heteropolytungstate, mullite, boehmite, titania, zirconia, magnesia, boria, zinc oxide, silica-titania, silica-zirconia, a mixed oxide thereof, or any mixture thereof. According to another aspect, the solid oxide of the chemically-modified solid oxide comprises or is selected from $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SbO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof, coated oxides thereof, and any combinations thereof.

The solid oxides described herein can be chemically treated with at least one electron withdrawing anion to provide the activator. For example, the at least one electron withdrawing anion can comprise or can be selected from fluoride, chloride, bromide, iodide, trifluoroacetate, sulfate, bisulfate, fluorosulfate, a $C_1$-$C_{10}$ alkyl sulfonate (for example, mesylate or methanesulfonate), a $C_6$-$C_{14}$ aryl sulfonate (for example, tosylate or toluenesulfonate), a $C_1$-$C_{10}$ fluoroalkyl sulfonate (for example, triflate or trifluoromethanesulfonate), a $C_6$-$C_{14}$ fluoroaryl sulfonate (for example, for example, $[CF_3C_6H_4SO_3]^-$), thiosulfate, fluoroborate, phosphate, fluorophosphates (monofluorophosphate and/or difluorophosphate), fluorozirconate, fluorotitanate, phosphotungstate, or similar anions, or any combination thereof.

In an aspect, for example, the chemically-modified solid oxide can comprise a solid oxide that is chemically modified with an electron-withdrawing anion, and wherein the electron-withdrawing anion comprises or is selected from sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof. In a further aspect, the chemically-modified solid oxide can be generated by treatment of a solid oxide with sulfuric acid, sulfate ion, bisulfate ion, fluorosulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

By way of example, in the process according to this disclosure, the chemically-modified solid oxide can comprises, can consist of, can consist essentially of, or can be selected from fluorided alumina, chlorided alumina, bromided alumina, fluorided-chlorided alumina, sulfated alumina, fluorided silica-alumina, chlorided silica-alumina, bromided silica-alumina, fluorided-chlorided silica-alumina, sulfated silica-alumina, fluorided silica-titania, chlorided silica-titania, bromided silica-titania, fluorided-chlorided silica-titania, sulfated silica-titania, fluorided silica-zirconia, chlorided silica-zirconia, bromided silica-zirconia, fluorided-chlorided silica-zirconia, sulfated silica-zirconia, fluorided silica-coated alumina, chlorided silica-coated alumina, bromided silica-coated alumina, fluorided-chlorided silica-coated alumina, sulfated silica-coated alumina, fluorided mullite, chlorided mullite, bromided mullite, fluorided-chlorided mullite, or sulfated mullite.

In other aspects, for example, in the process according to this disclosure the chemically-modified solid oxide can comprise, can consist of, can consist essentially of, or can be selected from a bisulfated, a fluorosulfated, a phosphated, a fluorophosphated, a $C_1$-$C_{10}$ alkyl sulfonated, a $C_6$-$C_{14}$ aryl sulfonated, a $C_1$-$C_{10}$ fluoroalkyl sulfonated, a $C_6$-$C_{14}$ fluoroaryl sulfonated, or a thio sulfated solid oxide, or a combination thereof, wherein the solid oxide is selected independently from alumina, silica-alumina, silica-titania, silica-zirconia, silica-coated alumina, mullite, or a combination thereof.

In another aspect and in any embodiment of this disclosure, for example, the chemically-modified solid oxide can comprise at least one silica-coated alumina treated with at least one electron-withdrawing anion, wherein: the at least one silica-coated alumina has a weight ratio of alumina to silica in a range from about 1:1 to about 100:1, and the at least one electron-withdrawing anion comprises fluoride, chloride, bromide, phosphate, triflate, bisulfate, sulfate, or any combination thereof.

In a further aspect, the chemically-modified solid oxide comprises, consists of, consists essentially of silica-coated alumina that has been fluorided and chlorided. In this aspect, the silica-coated alumina can comprise from about 10 to about 80 wt. % silica, based on the weight of the silica-coated alumina; the fluorided-chlorided silica-coated alumina comprises from about 2 to about 15 wt. % F, based on the weight of the fluorided-chlorided silica-coated alumina; and/or the fluorided-chlorided silica-coated alumina comprises from about 1 to about 10 wt. % Cl, based on the weight of the fluorided-chlorided silica-coated alumina. In this process, the fluorided-chlorided silica-coated alumina can be produced by a process comprising: (a) calcining a silica-coated alumina at a peak calcining temperature to produce a calcined silica-coated alumina; (b) contacting the calcined silica-coated alumina with a chlorine-containing compound and calcining at a peak chloriding temperature to produce a chlorided silica-coated alumina; and (c) contacting the chlorided silica-coated alumina with a fluorine-containing compound and calcining at a peak fluoriding temperature to produce the fluorided-chlorided silica-coated alumina. The fluorided-chlorided silica-coated alumina can have, for example, a pore volume in a range from about 0.9 to about 2.0 mL/g; and a surface area in a range from about 200 to about 700 m$^2$/g.

In yet a further aspect and in any embodiment of this disclosure, the chemically-modified solid oxide can comprise the contact product of at least one solid oxide compound and at least one electron-withdrawing anion source. The solid oxide compound and electron-withdrawing anion source are described independently herein and may be utilized in any combination to further describe the chemically-modified solid oxide comprising the contact product of at least one solid oxide compound and at least one electron-withdrawing anion source. That is, the chemically-modified solid oxide is provided upon contacting or treating the solid oxide with the electron-withdrawing anion source. In an aspect, the solid oxide compound can comprise or can be selected from an inorganic oxide.

In an aspect, the solid oxide compound can be calcined prior to contacting with the electron-withdrawing anion source, though this is not required. In another aspect, the solid oxide compound can be calcined during or after contacting with the electron-withdrawing anion source. Thus, contact product of the solid oxide and the electron-withdrawing anion may be calcined either during or after the solid oxide compound is contacted with the electron-withdrawing anion source. In this aspect, the solid oxide compound may be calcined or uncalcined. In another aspect, the activator may comprise the contact product of at least one calcined solid oxide compound and at least one electron-withdrawing anion source.

While not intending to be bound by theory, the chemically-modified solid oxide is thought to function as a co-catalyst or activator when used as disclosed herein. Moreover, the chemically-modified solid oxide is thought to function as a better co-catalyst or activator as compared to the non-chemically-modified oxide. The activation function of the chemically-modified solid oxide is evident in the enhanced activity of activator as a whole, as compared to an activator containing the corresponding untreated solid oxide.

In one aspect, the chemically-modified solid oxide of this disclosure can comprise a solid inorganic oxide material, a mixed oxide material, or a combination of inorganic oxide materials, that is chemically-modified with an electron-withdrawing component, and optionally treated with a metal. Thus, the solid oxide of this disclosure encompasses oxide materials such as alumina, "mixed oxide" compounds thereof such as silica-alumina, and combinations and mixtures thereof. The mixed oxide compounds such as silica-alumina can be single or multiple chemical phases with more than one metal combined with oxygen to form a solid oxide compound, and are encompassed by this disclosure. The solid inorganic oxide material, mixed oxide material, combination of inorganic oxide materials, electron-withdrawing component, and optional metal are independently described herein and may be utilized in any combination to further described the chemically-modified solid oxide.

In one aspect of this disclosure, the chemically-modified solid oxide further can comprise a metal or metal ion selected from zinc, nickel, vanadium, titanium, silver, copper, gallium, tin, tungsten, molybdenum, or any combination thereof; alternatively, the chemically-modified solid oxide further can comprise a metal or metal ion selected from zinc, nickel, vanadium, titanium, or tin, or any combination thereof; alternatively, the chemically-modified solid oxide can further comprise a metal or metal ion selected from zinc, nickel, vanadium, tin, or any combination thereof.

Examples of chemically-modified solid oxides that further comprise a metal or metal ion include, but are not limited to, zinc-impregnated chlorided alumina, titanium-impregnated fluorided alumina, zinc-impregnated fluorided alumina, zinc-impregnated chlorided silica-alumina, zinc-impregnated fluorided silica-alumina, zinc-impregnated sulfated alumina, chlorided zinc aluminate, fluorided zinc aluminate, sulfated zinc aluminate, or any combination thereof; alternatively, the chemically-modified solid oxide can be selected from fluorided alumina, chlorided alumina, sulfated alumina, fluorided silica-alumina, chlorided silica-alumina, sulfated silica-alumina, fluorided silica-zirconia, sulfated silica-zirconia, or any combination thereof.

In one aspect, the chemically-modified solid oxide can comprise a solid inorganic oxide comprising oxygen and at least one element selected from Group 2, 3, 4, 5, 6, 7, 8, 9, 10, 11, 12, 13, 14, or 15 of the periodic table, or comprising oxygen and at least one element selected from the lanthanide or actinide elements; alternatively, the chemically-modified solid oxide can comprise a solid inorganic oxide comprising oxygen and at least one element selected from Group 4, 5, 6, 12, 13, or 14 of the periodic table, or comprising oxygen and at least one element selected from the lanthanide elements. (See: *Hawley's Condensed Chemical Dictionary*, 11$^{th}$ Ed., John Wiley & Sons; 1995; Cotton, F. A.; Wilkinson, G.; Murillo; C. A.; and Bochmann; M. *Advanced Inorganic Chemistry*, 6$^{th}$ Ed., Wiley-Interscience, 1999.) Usually, the inorganic oxide can comprise oxygen and at least one element selected from Al, B, Be, Bi, Cd, Co, Cr, Cu, Fe, Ga, La, Mn, Mo, Ni, Sb, Si, Sn, Sr, Th, Ti, V, W, P, Y, Zn or Zr; alternatively, the inorganic oxide can comprise oxygen and at least one element selected from Al, B, Si, Ti, P, Zn or Zr.

Suitable examples of solid oxide materials or compounds that can be used in the chemically-modified solid oxide of the present disclosure include, but are not limited to, Al$_2$O$_3$, B$_2$O$_3$, BeO, Bi$_2$O$_3$, CdO, Co$_3$O$_4$, Cr$_2$O$_3$, CuO, Fe$_2$O$_3$, Ga$_2$O$_3$, La$_2$O$_3$, Mn$_2$O$_3$, MoO$_3$, NiO, P$_2$O$_5$, Sb$_2$O$_5$, SiO$_2$, SnO$_2$, SrO, ThO$_2$, TiO$_2$, V$_2$O$_5$, WO$_3$, Y$_2$O$_3$, ZnO, ZrO$_2$, and the like, including mixed oxides thereof, and combinations thereof; alternatively, suitable examples of solid oxide materials or compounds that can be used in the chemically-modified solid oxide of the present disclosure include, but are not limited to, Al$_2$O$_3$, B$_2$O$_3$, SiO$_2$, SnO$_2$, TiO$_2$, V$_2$O$_5$, WO$_3$, Y$_2$O$_3$, ZnO, ZrO$_2$, and the like, including mixed oxides thereof, and combinations thereof; alternatively, suitable examples of solid oxide materials or compounds that can be used in the chemically-modified solid oxide of the present disclosure include, but are not limited to, Al$_2$O$_3$, SiO$_2$, TiO$_2$, ZrO$_2$, and the like, including mixed oxides thereof, and combinations thereof.

Examples of mixed oxides that can be used in the activator of the present disclosure include, but are not limited to, silica-alumina, silica-titania, silica-zirconia, zeolites, clay minerals, silica-coated alumina, aluminum phosphate, aluminophosphate, heteropolytungstate, mullite, boehmite, alumina-titania, alumina-zirconia, zinc-aluminate and the like; alternatively, examples of mixed oxides that can be used in the activator of the present disclosure include, but are not limited to, silica-alumina, silica-titania, silica-zirconia, alumina-titania, alumina-zirconia, zinc-aluminate and the like; alternatively, examples of mixed oxides that can be used in the activator of the present disclosure include, but are not limited to, silica-alumina, silica-titania, silica-zirconia, alumina-titania, and the like.

In one aspect of this disclosure, the solid oxide material is chemically-modified by contacting it with at least one electron-withdrawing component, typically an electron-withdrawing anion source. Further, the solid oxide material can be chemically-modified with a metal ion if desired, then calcining to form a metal-containing or metal-impregnated chemically-modified solid oxide. Alternatively, a solid oxide material and an electron-withdrawing anion source are contacted and calcined simultaneously. The method by which the oxide is contacted with an electron-withdrawing component, typically a salt or an acid of an electron-withdrawing anion, includes, but is not limited to, gelling, co-gelling, impregnation of one compound onto another, and the like. Typically, following any contacting method, the contacted mixture of oxide compound, electron-withdrawing anion, and the metal ion if present can be calcined.

Without being bound by theory, the electron-withdrawing component used to treat the oxide can be any component that increases the Lewis or Brønsted acidity of the solid oxide upon treatment. In one aspect, the electron-withdrawing component is an electron-withdrawing anion derived from a salt, an acid, or other compound such as a volatile organic compound that may serve as a source or precursor for that anion. Examples of electron-withdrawing anions include, but are not limited to, sulfate, bisulfate, fluoride, chloride, bromide, iodide, fluoro sulfate, fluoroborate, phosphate, fluorophosphate, trifluoroacetate, triflate, fluorozirconate, fluorotitanate, trifluoroacetate, triflate, and the like, including mixtures and combinations thereof; alternatively, examples of electron-withdrawing anions include, but are not limited to, sulfate, bisulfate, fluoride, chloride, fluoro sulfate, fluoroborate, phosphate, fluorophosphate, trifluoroacetate, triflate, fluorozirconate, fluorotitanate, and the like, including mixtures and combinations thereof; alternatively, examples of electron-withdrawing anions include, but are not limited to, fluoride, sources of fluoride, chloride, bisulfate, sulfate, and the like, including mixtures and combinations thereof. In addition, other ionic or non-ionic compounds that serve as sources for these electron-withdrawing anions may also be employed in the present disclosure.

When the electron-withdrawing component can comprise a salt of an electron-withdrawing anion, the counterion or cation of that salt may be selected from any cation that allows the salt to revert or decompose back to the acid during calcining. Factors that dictate the suitability of the particular salt to serve as a source for the electron-withdrawing anion include, but are not limited to, the solubility of the salt in the desired solvent, the lack of adverse reactivity of the cation, ion-pairing effects between the cation and anion, hygroscopic properties imparted to the salt by the cation, and the like, and thermal stability of the anion. Examples of suitable cations in the salt of the electron-withdrawing anion include, but are not limited to, ammonium, trialkyl ammonium, tetraalkyl ammonium, tetraalkyl phosphonium, $H^+$, $[H(OEt_2)_2]^+$, and the like; alternatively, ammonium; alternatively, trialkyl ammonium; alternatively, tetraalkyl ammonium; alternatively, tetraalkyl phosphonium; or alternatively, $H^+$, $[H(OEt_2)_2]^+$.

Further, combinations of one or more different electron-withdrawing anions, in varying proportions, can be used to tailor the specific activity of the chemically-modified solid oxide to the desired level. Combinations of electron-withdrawing components may be contacted with the oxide material simultaneously or individually, and any order that affords the desired chemically-modified solid oxide acidity. For example, one aspect of this disclosure is employing two or more electron-withdrawing anion source compounds in two or more separate contacting steps. Thus, one example of such a process by which an chemically-modified solid oxide is prepared is as follows: a selected solid oxide compound, or combination of oxide compounds, is contacted with a first electron-withdrawing anion source compound to form a first mixture, this first mixture is then calcined, the calcined first mixture is then contacted with a second electron-withdrawing anion source compound to form a second mixture, followed by calcining said second mixture to form a treated solid oxide compound. In such a process, the first and second electron-withdrawing anion source compounds are typically different compounds, although they may be the same compound.

In one aspect of the disclosure, the chemically-modified solid oxide may be produced by a process comprising:
1) contacting a solid oxide compound with at least one electron-withdrawing anion source compound to form a first mixture; and
2) calcining the first mixture to form the chemically-modified solid oxide.

In another aspect of this disclosure, the chemically-modified solid oxide can be produced by a process comprising:
1) contacting at least one solid oxide compound with a first electron-withdrawing anion source compound to form a first mixture; and
2) calcining the first mixture to produce a calcined first mixture;
3) contacting the calcined first mixture with a second electron-withdrawing anion source compound to form a second mixture; and
4) calcining the second mixture to form the chemically-modified solid oxide.

Thus, the solid oxide activator-support is sometimes referred to simply as a treated solid oxide compound.

In one aspect of this disclosure, once the solid oxide has been treated and dried, it may be subsequently calcined. Calcining the chemically treated solid oxide is generally conducted in an ambient atmosphere; alternatively, in a dry ambient atmosphere. The solid oxide may be calcined at a temperature from about 200° C. to about 900° C.; alternatively, from about 300° C. to about 800° C.; alternatively, from about 400° C. to about 700° C.; or alternatively, from about 350° C. to about 550° C. The period of time at which the solid oxide is maintained at the calcining temperature may be about 1 minute to about 100 hours; alternatively, from about 1 hour to about 50 hours; alternatively, from about 3 hours to about 20 hours; or alternatively, from about 1 to about 10 hours.

Further, any type of suitable ambient atmosphere can be used during calcining. Generally, calcining is conducted in an oxidizing atmosphere, such as air. Alternatively, an inert atmosphere, such as nitrogen or argon, or a reducing atmosphere such as hydrogen or carbon monoxide, may be used.

In another aspect of the disclosure, the solid oxide component used to prepare the chemically-modified solid oxide has a pore volume greater than about 0.1 cc/g. In another aspect, the solid oxide component has a pore volume greater than about 0.5 cc/g, and in yet another aspect, greater than about 1.0 cc/g. In still another aspect, the solid oxide component has a surface area from about 100 $m^2/g$ to about 1000 $m^2/g$. In another aspect, solid oxide component has a surface area from about 200 $m^2/g$ to about 800 $m^2/g$, and in still another aspect, from about 250 $m^2/g$ to about 600 $m^2/g$.

The solid oxide material may be treated with a source of halide ion or sulfate ion, or a combination of anions, and optionally treated with a metal ion, then calcined to provide the chemically-modified solid oxide in the form of a particulate solid. In one aspect, the solid oxide material is treated with a source of sulfate, termed a sulfating agent, a source of chloride ion, termed a chloriding agent, a source of fluoride ion, termed a fluoriding agent, or a combination thereof, and calcined to provide the solid oxide activator.

In one aspect, the chemically-modified solid oxide can comprise a fluorided solid oxide in the form of a particulate solid, thus a source of fluoride ion is added to the oxide by treatment with a fluoriding agent. In still another aspect, fluoride ion may be added to the oxide by forming a slurry of the oxide in a suitable solvent such as alcohol or water, including, but are not limited to, the one to three carbon alcohols because of their volatility and low surface tension. Examples of fluoriding agents that can be used in this disclosure include, but are not limited to, hydrofluoric acid (HF), ammonium fluoride ($NH_4F$), ammonium bifluoride ($NH_4HF_2$), ammonium tetrafluoroborate ($NH_4BF_4$), ammonium silicofluoride (hexafluorosilicate) (($NH_4)_2SiF_6$), ammonium hexafluorophosphate ($NH_4PF_6$), analogs thereof, and combinations thereof; alternatively, hydrofluoric acid (HF), ammonium fluoride ($NH_4F$), ammonium bifluoride ($NH_4HF_2$), ammonium tetrafluoroborate ($NH_4BF_4$), analogs thereof, and combinations thereof. For example, ammonium bifluoride $NH_4HF_2$ may be used as the fluoriding agent, due to its ease of use and ready availability.

In another aspect of the present disclosure, the solid oxide can be treated with a fluoriding agent during the calcining step. Any fluoriding agent capable of thoroughly contacting the solid oxide during the calcining step can be used. For example, in addition to those fluoriding agents described previously, volatile organic fluoriding agents may be used. Examples of volatile organic fluoriding agents useful in this aspect of the disclosure include, but are not limited to, freons, perfluorohexane, perfluorobenzene, fluoromethane, trifluoroethanol, and combinations thereof. Gaseous hydrogen fluoride or fluorine itself can also be used with the solid oxide is fluorided during calcining. One convenient method of contacting the solid oxide with the fluoriding agent is to vaporize a fluoriding agent into a gas stream used to fluidize the solid oxide during calcination.

Similarly, in another aspect of this disclosure, the chemically-modified solid oxide can comprise a chlorided solid oxide in the form of a particulate solid, thus a source of chloride ion is added to the oxide by treatment with a chloriding agent. The chloride ion may be added to the oxide by forming a slurry of the oxide in a suitable solvent. In another aspect of the present disclosure, the solid oxide can be treated with a chloriding agent during the calcining step. Any chloriding agent capable of serving as a source of chloride and thoroughly contacting the oxide during the calcining step can be used. For example, volatile organic chloriding agents may be used. Examples of volatile organic chloriding agents useful in this aspect of the disclosure include, but are not limited to, certain freons, perchlorobenzene, chloromethane, dichloromethane, chloroform, carbon tetrachloride, trichloroethanol, or any combination thereof. Gaseous hydrogen chloride or chlorine itself can also be used with the solid oxide during calcining. One convenient method of contacting the oxide with the chloriding agent is to vaporize a chloriding agent into a gas stream used to fluidize the solid oxide during calcination.

In one aspect, the amount of fluoride or chloride ion present before calcining the solid oxide is generally from about 2 to about 50% by weight, where the weight percents are based on the weight of the solid oxide, for example silica-alumina, before calcining. In another aspect, the amount of fluoride or chloride ion present before calcining the solid oxide is from about 3 to about 25% by weight, and in another aspect, from about 4 to about 20% by weight. Once impregnated with halide, the halided oxide may be dried by any method known in the art including, but not limited to, suction filtration followed by evaporation, drying under vacuum, spray drying, and the like, although it is also possible to initiate the calcining step immediately without drying the impregnated solid oxide.

In an aspect, silica-alumina may be utilized as the solid oxide material. The silica-alumina used to prepare the treated silica-alumina can have a pore volume greater than about 0.5 cc/g. In one aspect, the pore volume may be greater than about 0.8 cc/g, and in another aspect, the pore volume may be greater than about 1.0 cc/g. Further, the silica-alumina may have a surface area greater than about 100 $m^2$/g. In one aspect, the surface area is greater than about 250 $m^2$/g, and in another aspect, the surface area may be greater than about 350 $m^2$/g. Generally, the silica-alumina of this disclosure has an alumina content from about 5 to about 95%. In one aspect, the alumina content of the silica-alumina may be from about 5 to about 50%, and in another aspect, the alumina content of the silica-alumina may be from about 8% to about 30% alumina by weight. In yet another aspect, the solid oxide component can comprise alumina without silica and in another aspect, the solid oxide component can comprise silica without alumina.

The sulfated solid oxide can comprise sulfate and a solid oxide component such as alumina or silica-alumina, in the form of a particulate solid. The sulfated oxide can be further treated with a metal ion if desired such that the calcined sulfated oxide can comprise a metal. In one aspect, the sulfated solid oxide can comprise sulfate and alumina. In one aspect of this disclosure, the sulfated alumina is formed by a process wherein the alumina is treated with a sulfate source, for example selected from, but not limited to, sulfuric acid or a sulfate salt such as ammonium sulfate. In one aspect, this process may be performed by forming a slurry of the alumina in a suitable solvent such as alcohol or water, in which the desired concentration of the sulfating agent has been added. Suitable organic solvents include, but are not limited to, the one to three carbon alcohols because of their volatility and low surface tension.

In one aspect of the disclosure, the amount of sulfate ion present before calcining is generally from about 0.5 parts by weight to about 100 parts by weight sulfate ion to about 100 parts by weight solid oxide. In another aspect, the amount of sulfate ion present before calcining is generally from about 1 part by weight to about 50 parts by weight sulfate ion to about 100 parts by weight solid oxide, and in still another aspect, from about 5 parts by weight to about 30 parts by weight sulfate ion to about 100 parts by weight solid oxide. These weight ratios are based on the weight of the solid oxide before calcining. Once impregnated with sulfate, the sulfated oxide may be dried by any method known in the art including, but not limited to, suction filtration followed by evaporation, drying under vacuum, spray drying, and the like, although it is also possible to initiate the calcining step immediately.

In addition to being treated with an electron-withdrawing component (for example, halide or sulfate ion), the solid inorganic oxide of this disclosure can be treated with a metal source if desired, including metal salts or metal-containing compounds. In one aspect of the disclosure, these compounds may be added to or impregnated onto the solid oxide in solution form, and subsequently converted into the supported metal upon calcining. The solid oxide may be treated with metal salts or metal-containing compounds before, after, or at the same time that the solid oxide is treated with the electron-withdrawing anion.

Further, any method of impregnating the solid oxide material with a metal may be used. The method by which the oxide is contacted with a metal source, typically a salt or metal-containing compound, includes, but is not limited to, gelling, co-gelling, impregnation of one compound onto another, and the like. Following any contacting method, the contacted mixture of oxide compound, electron-withdrawing anion, and the metal ion is typically calcined. Alternatively, a solid oxide material, an electron-withdrawing anion source, and the metal salt or metal-containing compound are contacted and calcined simultaneously.

Various processes to prepare solid oxide activator-supports that can be employed in this disclosure have been reported. For example, U.S. Pat. Nos. 6,107,230, 6,165,929, 6,294,494, 6,300,271, 6,316,553, 6,355,594, 6,376,415, 6,391,816, 6,395,666, 6,524,987, 6,548,441, 6,750,302, 6,831,141, 6,936,667, 6,992,032, 7,601,665, 7,026,494, 7,148,298, 7,470,758, 7,517,939, 7,576,163, 7,294,599, 7,629,284, 7,501,372, 7,041,617, 7,226,886, 7,199,073, 7,312,283, 7,619,047, 7,884,163, 8,703,886, and 9,023,959 describe such methods, each of which is incorporated by reference herein, in pertinent part.

Metal-Treated Chemically-Modified Solid Oxide (MT-CMSO)

In an aspect, the disclosed processes for producing α,β-unsaturated carboxylic acids or salts thereof utilize as an activator a chemically-modified solid oxide which has been metal treated. For example, the chemically-modified solid oxides disclosed herein, for example, sulfur oxoacid anion-modified solid oxides, phosphorus oxoacid anion-modified solid oxides, or a halide ion-modified solid oxides, can be further chemically treated with a source of a metal cation, for example, a metal cation comprising or selected from a Group 1, 2, 12 or 13 metal.

As disclosed herein, the chemically-modified solid oxide (CMSO) can be a metal-treated chemically-modified solid oxide (MT-CMSO). For example, metal-treated chemically-modified solid oxides can be produced by, for example, contacting any suitable solid oxide and any suitable electron-withdrawing anion as disclosed herein and calcining (concurrently and/or subsequently) to form the chemically-modified solid oxide CMSO. The CMSO is then contacted with any suitable source of the metal, that is, a metal cation source. For example, suitable metals for treating the CMSO to form the MT-CMSO include, but are not limited to, Group 1 (alkali) metals, Group 2 (alkaline earth) metals, Group 12 metals, and/or Group 13 metals, including any combination thereof. Optionally, a further calcining step can be used.

The metal-treated chemically-modified solid oxide can comprise an alkali metal, an alkaline earth metal, a transition metal, or any combination thereof (e.g., a transition metal and an alkali metal). When the metal-treated chemically-modified solid oxide comprises an alkali metal, the treated solid oxide can be referred to as an alkali metal-treated chemically-modified solid oxide, and the alkali metal often comprises sodium, potassium, or cesium, either singly or in combination. When the metal-treated chemically-modified solid oxide comprises an alkaline earth metal, the treated solid oxide can be referred to as an alkaline earth metal-treated chemically-modified solid oxide, and the alkaline earth metal often comprises magnesium, calcium, or barium, either singly or in combination.

Illustrative and non-limiting examples of metal-treated chemically-modified solid oxides can include sodium-treated chlorided alumina, sodium-treated sulfated alumina, sodium-treated sulfated silica-coated alumina, sodium-treated fluorided silica-coated alumina, sodium-treated fluorided silica-alumina, sodium-treated fluorided-chlorided silica-coated alumina, and the like, as well as combinations thereof.

The MT-CMSO can be prepared from the CMSO as shown in Scheme 1, which illustrates the regeneration of the MT-CMSO from the CMSO, namely by either [1] treatment of the CMSO with a metal-containing base such as a metal hydroxide or metal alkoxide, or metal alkyl amide, 7A, or [2] treatment of the CMSO with an acid and a metal salt, for example, a combination of $H_2SO_4$ and NaCl, 7B. While not intending to be theory-bound, the resulting MT-CMSO is believed to have accessible metal sites that are capable of interacting with the metalalactone, for example, as illustrated in Scheme 1. Also while not intending to be bound by theory, the CMSO is generally a Lewis acidic solid oxide ("solid super acid"), which forms when a solid oxide is treated with an electron-withdrawing anion in acid form or salt form, in which cation of the salt form reverts or decomposes back to the acid during calcining. Thus, it is believed that treatment of the acidic CMSO with a metal-containing base such as a metal hydroxide or metal alkoxide forms the metallated form of the CMSO referred to herein as the MT-CMSO. Alternatively, treatment of the acidic CMSO with an acid such as $H_2SO_4$ and a metal salt such as NaCl, can also be used to form the MT-CMSO.

In one aspect, the metal-treated chemically-modified solid oxide can be prepared by [a] contacting a solid oxide with a sulfur oxoacid anion, a phosphorus oxoacid anion, or a halide ion to provide the chemically-modified solid oxide, followed by [b] contacting the chemically-modified solid oxide with [1] a metal-containing base or [2] a metal-containing salt in combination with an acid. In this aspect, the sulfur oxoacid anion can be provided by sulfuric acid or a sulfate salt, the phosphorus oxoacid anion can be provided by phosphoric acid or a phosphate salt, and the halide ion can be provided by a hydrohalic acid or a halide salt. In a similar manner, once the reaction mixture has been subjected to reaction conditions suitable to form the α,β-unsaturated carboxylic acid or the salt thereof, the remaining oxide co-catalyst can be regenerated to the metal-treated chemically-modified solid oxide, by, for example, contacting the solid oxide remaining following the elimination step with [1] a metal-containing base or [2] a metal-containing salt in combination with an acid. For example, referring again to Scheme 1, the CMSO can be regenerated to the MT-CMSO by either [1] treatment with a metal-containing base such as a metal hydroxide or metal alkoxide, or metal alkyl amide, 7A, or [2] treatment with an acid and a metal salt, for example, a combination of $H_2SO_4$ and NaCl, 7B.

According to an aspect, the metal-treated chemically-modified solid oxide can comprise any suitable Lewis acidic metal cation or any Lewis acidic metal cation disclosed herein. In one aspect, the metal-treated chemically-modified solid oxide can comprise a metal cation selected from a Group 1, 2, 12 or 13 metal. The metal-treated chemically-modified solid oxide can comprise an alkali metal cation, an alkaline earth metal cation, or any combination thereof. In another aspect, the metal-treated chemically-modified solid oxide can comprise at least one cation selected from lithium, sodium, potassium, rubidium, cesium, magnesium, calcium, strontium, barium, copper, zinc, aluminum, or gallium. In particular, the metal-treated chemically-modified solid oxide can comprise sodium ions or potassium ions.

As described herein, the metal-treated chemically-modified solid oxide can be prepared by contacting the chemically-modified solid oxide with [a] a metal-containing base or [b] a metal-containing salt in combination with an acid. Depending upon the specific solid oxide and electron withdrawing anion that are combined to provide the chemically-modified solid oxide (CMSO), some of the metal-containing bases used in method [a] for some CMSO treatments can also be used as metal-containing salts in method [b] of this preparation method.

In one aspect, the metal-containing base that can be used to convert the CMSO to the MT-CMSO according to method [a] above can comprise or can be selected from any suitable base or any base disclosed herein, e.g., carbonates (e.g., $Na_2CO_3$, $K_2CO_3$, $Cs_2CO_3$, $CaCO_3$, $MgCO_3$), hydroxides (e.g., NaOH, KOH, $Mg(OH)_2$), alkoxides (e.g., $Na(O^tBu)$, $K(O^tBu)$, $Mg(OEt)_2$, $Al(O^iPr)_3$), aryloxides (e.g. $Na(OC_6H_5)$, $K(OC_6H_5)$, sulfates (e.g. $Na_2SO_4$, $K_2SO_4$, $CaSO_4$, $MgSO_4$), and phosphates (e.g. $Na_3PO_4$, $K_3PO_4$), and the like.

According to another aspect, the metal-containing bases can comprise or can be selected from alkali metal hydroxides or alkali metal alkoxides. In one aspect, the metal-containing bases can comprise or can be selected from alkali metal alkoxide, aryloxide, amide, alkyl amide, or arylamide, compounds or the like. In another aspect, metal-containing bases can comprise or can be selected from a metal-containing alkoxide, an aryloxide, an alkylamide, an arylamide, a hydride, or a polyhydride, and/or substituted analogs thereof. Further, the metal-containing bases used according to this disclosure can be absent any specific metal-containing alkoxide, aryloxide, alkylamide, arylamide, hydride, or polyhydride, and/or substituted analogs thereof. For example, the metal-containing base can be absent a hydride compound such as NaH or KH. In another aspect, the MT-CMSO can be generated by contacting a CMSO with a metal-containing base, wherein the metal-containing base is absent sodium hydride, an aryloxide salt (such as a sodium aryloxide), an alkoxide salt (such as a sodium tert-butoxide), and/or a phosphazene.

In a further aspect, the metal-containing salt that can be used to convert the CMSO to the MT-CMSO in combination with the acid according to method [b] above can comprise or can be selected from any suitable metal-containing salt or any metal-containing salt disclosed herein, e.g. chlorides (e.g. NaCl, KCl, RbCl, $CaCl_2$, $MgCl_2$), bisulfates (e.g. $NaHSO_4$, $KHSO_4$, $Ca(HSO_4)_2$, $Mg(HSO_4)_2$), fluoro sulfates (e.g. $NaSO_3F$, $KSO_3F$, $RbSO_3F$, $CsSO_3F$), hydrogen phosphates (e.g. $Na_2HPO_4$, $K_2HPO_4$), fluorophosphates (e.g. $Na_2PO_3F$, $K_2PO_3F$, $Cs_2PO_3F$, $CaPO_3F$, $MgPO_3F$), triflates (e.g $NaSO_3CF_3$, $KSO_3CF_3$), mesylates (e.g. $NaSO_3CH_3$, $KSO_3CH_3$), tosylates (e.g. $NaSO_3C_6H_4CH_3$, $KSO_3C_6H_4CH_3$), thiosulfates (e.g. $Na_2S_2O_3$, $K_2S_2O_3$), $C_1$-$C_{10}$ alkyl sulfonates (e.g. $NaSO_3R$, $KSO_3R$, wherein R is a $C_1$-$C_{10}$ alkyl), $C_6$-$C_{14}$ aryl sulfonates (e.g. $NaSO_3Ar$, $KSO_3Ar$, wherein Ar is a $C_6$-$C_{14}$ aryl), and the like.

In a further aspect, the acid that can be used to convert the CMSO to the MT-CMSO in combination with the metal-containing salt according to method [b] above can comprise or can be selected from any suitable acid or any acid disclosed herein, e.g. sulfuric acid, hydrochloric acid, fluoro sulfuric acid, phosphoric acid, fluorophosphoric acid, triflic (trifluoromethane-sulfonic) acid, methanesulfonic acid, toluenesulfonic acid, $C_1$-$C_{10}$ alkyl sulfonic acid, $C_6$-$C_{14}$ aryl sulfonic acid, and the like, including any combination thereof.

In an aspect, in the processes described herein, the metal-treated chemically-modified solid oxide can be produced by a process comprising contacting any suitable chemically-modified solid oxide or any chemically-modified solid oxide disclosed herein and any suitable metal-containing compound or any metal-containing compound disclosed herein to provide a mixture, and concurrently and/or subsequently drying and/or calcining the mixture. In an aspect, the metal-treated chemically-modified solid oxide can be produced by a process comprising contacting any suitable solid oxide with an electron-withdrawing anion to form a first mixture and concurrently and/or subsequently drying and/or calcining the first mixture, followed by contacting the dried and/or calcined first mixture with any suitable metal-containing compound to provide a second mixture, and concurrently and/or subsequently drying and/or calcining the second mixture. According to another aspect, the metal-treated chemically-modified solid oxide can be produced by a process comprising contacting any suitable solid oxide and any suitable electron-withdrawing anion and calcining (concurrently and/or subsequently) to form the chemically-modified solid oxide, and contacting the chemically-modified solid oxide with any suitable metal-containing compound.

The metal-treated chemically-modified solid oxide can comprise a chemically-modified solid oxide treated with an alkali metal, an alkaline earth metal, or any combination thereof in a total amount of from 1 wt. % to 30 wt. %, from 3 wt. % to 25 wt. %, or from 5 wt. % to 20 wt. %, based on the total weight of the metal-treated chemically-modified solid oxide. In another aspect, any metal present in the metal-treated chemically-modified solid oxide can be present in an amount of at least 0.5 wt. %, or at least 1 wt. %, and can be present in concentrations up to 30 wt. %, up to 25 wt. %, up to 20 wt. %, up to 15 wt. %, up to 12 wt. %, up to 10 wt. %, up to 8 wt. %, up to 7 wt. %, or up to up to 5 wt. %. For instance, the metal-treated chemically-modified solid oxide generally can contain from 1 wt. % to 25 wt. %, from 2 wt. % to 30 wt. %, from 2 wt. % to 25 wt. %, from 5 to 30 wt. %, from 5 wt. % to 25 wt. %, from 3 wt. % to 15 wt. %, from 5 wt. % to 12 wt. %, or from 6 wt. % to 18 wt. %, of the metal, based on the total weight of the metal-treated chemically-modified solid oxide.

Diluents

The processes disclosed herein typically are conducted in the presence of a diluent. Mixtures and combinations of diluents can be utilized in these processes. The diluent can comprise, consist essentially of, or consist of, any suitable solvent or any solvent disclosed herein, unless otherwise specified. For example, the diluent can comprise, consist essentially of, or consist of a non-protic solvent, a protic solvent, a non-coordinating solvent, or a coordinating solvent. For instance, in accordance with one aspect of this disclosure, the diluent can comprise a non-protic solvent. Representative and non-limiting examples of non-protic solvents can include tetrahydrofuran (THF), 2,5-$Me_2THF$, acetone, toluene, chlorobenzene, pyridine, acetonitrile, carbon dioxide, olefin, and the like, as well as combinations thereof. In accordance with another aspect, the diluent can comprise a weakly coordinating or non-coordinating solvent. Representative and non-limiting examples of weakly coordinating or non-coordinating solvents can include toluene, chlorobenzene, paraffins, halogenated paraffins, and the like, as well as combinations thereof.

In accordance with yet another aspect, the diluent can comprise a carbonyl-containing solvent, for instance, ketones, esters, amides, and the like, as well as combinations thereof. Representative and non-limiting examples of carbonyl-containing solvents can include acetone, ethyl methyl ketone, ethyl acetate, propyl acetate, butyl acetate, isobutyl isobutyrate, methyl lactate, ethyl lactate, N,N-dimethylformamide, and the like, as well as combinations thereof. In still another aspect, the diluent can comprise THF, 2,5-Me$_2$THF, methanol, acetone, toluene, chlorobenzene, pyridine, anisole, or a combination thereof; alternatively, THF; alternatively, 2,5-Me$_2$THF; alternatively, methanol; alternatively, acetone; alternatively, toluene; alternatively, chlorobenzene; or alternatively, pyridine.

In an aspect, the diluent can comprise (or consist essentially of, or consist of) an aromatic hydrocarbon solvent. Non-limiting examples of suitable aromatic hydrocarbon solvents that can be utilized singly or in any combination include benzene, toluene, xylene (inclusive of ortho-xylene, meta-xylene, para-xylene, or mixtures thereof), and ethylbenzene, or combinations thereof; alternatively, benzene; alternatively, toluene; alternatively, xylene; or alternatively, ethylbenzene.

In an aspect, the diluent can comprise (or consist essentially of, or consist of) a halogenated aromatic hydrocarbon solvent. Non-limiting examples of suitable halogenated aromatic hydrocarbon solvents that can be utilized singly or in any combination include chlorobenzene, dichlorobenzene, and combinations thereof; alternatively, chlorobenzene; or alternatively, dichlorobenzene.

In an aspect, the diluent can comprise (or consist essentially of, or consist of) an ether solvent. Non-limiting examples of suitable ether solvents that can be utilized singly or in any combination include dimethyl ether, diethyl ether, diisopropyl ether, di-n-propyl ether, di-n-butyl ether, diphenyl ether, methyl ethyl ether, methyl t-butyl ether, dihydrofuran, tetrahydrofuran (THF), 2,5-Me$_2$THF, 1,2-dimethoxyethane, 1,4-dioxane, anisole, and combinations thereof; alternatively, diethyl ether, dibutyl ether, THF, 2,5-Me$_2$THF, 1,2-dimethoxyethane, 1,4-dioxane, and combinations thereof; alternatively, THF; or alternatively, diethyl ether.

In a further aspect, any of these aforementioned diluents can be excluded from the diluent or diluent mixture. For example, the diluent can be absent a phenol or a substituted phenol, an alcohol or a substituted alcohol, an amine or a substituted amine, an ether, an aliphatic hydrocarbon solvent, an aromatic hydrocarbon solvent, an aldehyde or ketone, an ester or amide, and/or absent a halogenated aromatic hydrocarbon, or any substituted analogs of these diluents halogenated analogs, including any of the aforementioned diluents. Therefore, Applicant reserves the right to exclude any of the diluents provided herein.

The diluent can comprise carbon dioxide, and can also comprise CO$_2$ under pressure. The diluent also can comprise the α,β-unsaturated carboxylic acid or the salt thereof, formed in the process. The diluent can comprise any suitable non-protic solvent, any non-protic solvent disclosed herein, and/or carbon dioxide (CO$_2$) under pressure. The diluent can comprise any suitable non-protic solvent, any non-protic solvent disclosed herein, the olefin such as ethylene, and/or carbon dioxide (CO$_2$) under pressure. Specifically, the diluent can comprise the olefin such as ethylene and carbon dioxide (CO$_2$) under pressure. The diluent also can comprise any suitable weakly coordinating or non-coordinating solvent, or any weakly coordinating or non-coordinating solvent disclosed herein.

In all aspects and embodiments disclosed herein, the diluent can include or comprise carbon dioxide, olefin, or combinations thereof. At least a portion of the diluent can comprise the α,β-unsaturated carboxylic acid or the salt thereof, formed in the process.

Catalysts and Metalalactones

In this disclosure, the term transition metal precursor, transition metal compound, transition metal catalyst, transition metal precursor compound, carboxylation catalyst, transition metal precursor complex and similar terms refer to a chemical compound that serves as the precursor to the metalalactone, prior to the coupling of the olefin and carbon dioxide at the metal center of the transition metal precursor compound. Therefore, the metal of the transition metal precursor compound and the metal of the metalalactone are the same. In some aspects, some of the ligands of the transition metal precursor compound carry over and are retained by the metalalactone following the coupling reaction. In other aspects, the transition metal precursor compound loses its existing ligands, referred to herein as first ligands, in presence of additional ligands such as chelating ligands, referred to herein as second ligands, as the metalalactone is formed. Therefore, the metalalactone generally incorporates the second (added) ligand(s), though in some aspects, the metalalactone can comprise the first ligand(s) that were bound in the transition metal precursor compound.

According to an aspect, the transition metal catalyst or compound used in the processes can be used without being immobilized on a solid support. That is the transition metal catalyst can be used is its usual form which is soluble in most useful solvents, without being bonded to or supported on any insoluble support, such as an inorganic oxide or mixed oxide material.

A prototypical example of a transition metal precursor compound that loses its initial ligands in the coupling reaction in the presence of a second (added) ligand, wherein the metalalactone incorporates the second (added) ligand(s), is contacting Ni(COD)$_2$ (COD is 1,5-cyclooctadiene) with a diphosphine ligand such as 1,2-bis(dicyclohexylphosphino)ethane in a diluent in the presence of ethylene and CO$_2$ to form a nickelalactone with a coordinated 1,2-bis(dicyclohexylphosphino)ethane bidentate ligand.

According to an aspect of this disclosure, there is provided a process for forming an α,β-unsaturated carboxylic acid or a salt thereof, the process comprising:
 a) contacting in any order
  i) a transition metal precursor compound comprising at least one first ligand;
  ii) optionally, at least one second ligand;
  iii) an olefin;
  iv) carbon dioxide (CO$_2$);
  v) a diluent; and
  vi) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
 b) subjecting the reaction mixture to reaction conditions suitable to form the α,β-unsaturated carboxylic acid or the salt thereof.

In an aspect, the transition metal precursor compound (catalyst) can be present in the reaction mixture at a concentration of less than 0.2 mM (millimolar).

In another aspect, this disclosure provides a process for forming an α,β-unsaturated carboxylic acid or a salt thereof, the process comprising:
 a) contacting
  i) a metalalactone compound;
  ii) a diluent; and iii) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and b) subjecting the reaction mixture to reaction conditions suitable to form the α,β-unsaturated carboxylic acid or the salt thereof.

In an aspect, the metalalactone can be present in the reaction mixture at a concentration of less than 0.2 mM (millimolar). According to an aspect, this reaction mixture can comprise an adduct of the metalalactone and the metal-treated chemically-modified solid oxide.

Generally, the processes disclosed herein employ a metalalactone or a transition metal precursor compound or complex. The transition metal of the metalalactone, or of the transition metal precursor compound, can be a Group 3 to Group 8 transition metal or, alternatively, a Group 8 to Group 11 transition metal. In one aspect, for instance, the transition metal can be Fe, Co, Ni, Cu, Ru, Rh, Pd, Ag, Ir, Pt, or Au, while in another aspect, the transition metal can be Fe, Ni, or Rh. Alternatively, the transition metal can be Fe; alternatively, the transition metal can be Co; alternatively, the transition metal can be Ni; alternatively, the transition metal can be Cu; alternatively, the transition metal can be Ru; alternatively, the transition metal can be Rh; alternatively, the transition metal can be Pd; alternatively, the transition metal can be Ag; alternatively, the transition metal can be Ir; alternatively, the transition metal can be Pt; or alternatively, the transition metal can Au.

In particular aspects contemplated herein, the transition metal can be Ni. Hence, the metalalactone can be a nickelalactone and the transition metal precursor compound can be a Ni-ligand complex in these aspects.

The ligand of the metalalactone and/or of the transition metal precursor compound, can be any suitable neutral electron donor group and/or Lewis base. For instance, the suitable neutral ligands can include sigma-donor solvents that contain a coordinating atom (or atoms) that can coordinate to the transition metal of the metalalactone (or of the transition metal precursor compound). Examples of suitable coordinating atoms in the ligands can include, but are not limited to, O, N, S, and P, or combinations of these atoms. In some aspects consistent with this disclosure, the ligand can be a bidentate ligand.

In an aspect, the ligand used to form the metalalactone and/or the transition metal precursor compound can be an ether, an organic carbonyl, a thioether, an amine, a nitrile, or a phosphine. In another aspect, the ligand used to form the metalalactone or the transition metal precursor compound can be an acyclic ether, a cyclic ether, an acyclic organic carbonyl, a cyclic organic carbonyl, an acyclic thioether, a cyclic thioether, a nitrile, an acyclic amine, a cyclic amine, an acyclic phosphine, or a cyclic phosphine.

Suitable ethers can include, but are not limited to, dimethyl ether, diethyl ether, dipropyl ether, dibutyl ether, methyl ethyl ether, methyl propyl ether, methyl butyl ether, diphenyl ether, ditolyl ether, tetrahydrofuran, 2-methyltetrahydrofuran, 2,5-dimethyltetrahydrofuran, 2,3-dihydrofuran, 2,5-dihydrofuran, furan, benzofuran, isobenzofuran, dibenzofuran, tetrahydropyran, 3,4-dihydro-2H-pyran, 3,6-dihydro-2H-pyran, 2H-pyran, 4H-pyran, 1,3-dioxane, 1,4-dioxane, morpholine, and the like, including substituted derivatives thereof.

Suitable organic carbonyls can include ketones, aldehydes, esters, and amides, either alone or in combination, and illustrative examples can include, but are not limited to, acetone, acetophenone, benzophenone, N,N-dimethylformamide, N,N-dimethylacetamide, methyl acetate, ethyl acetate, and the like, including substituted derivatives thereof.

Suitable thioethers can include, but are not limited to, dimethyl thioether, diethyl thioether, dipropyl thioether, dibutyl thioether, methyl ethyl thioether, methyl propyl thioether, methyl butyl thioether, diphenyl thioether, ditolyl thioether, thiophene, benzothiophene, tetrahydrothiophene, thiane, and the like, including substituted derivatives thereof.

Suitable nitriles can include, but are not limited to, acetonitrile, propionitrile, butyronitrile, benzonitrile, 4-methylbenzonitrile, and the like, including substituted derivatives thereof.

Suitable amines can include, but are not limited to, methyl amine, ethyl amine, propyl amine, butyl amine, dimethyl amine, diethyl amine, dipropyl amine, dibutyl amine, trimethyl amine, triethyl amine, tripropyl amine, tributyl amine, aniline, diphenylamine, triphenylamine, tolylamine, xylylamine, ditolylamine, pyridine, quinoline, pyrrole, indole, 2-methylpyridine, 3-methylpyridine, 4-methylpyridine, 2,5-dimethylpyrrole, 2,5-diethylpyrrole, 2,5-dipropylpyrrole, 2,5-dibutylpyrrole, 2,4-dimethylpyrrole, 2,4-diethylpyrrole, 2,4-dipropylpyrrole, 2,4-dibutylpyrrole, 3,4-dimethylpyrrole, 3,4-diethylpyrrole, 3,4-dipropylpyrrole, 3,4-dibutylpyrrole, 2-methylpyrrole, 2-ethylpyrrole, 2-propylpyrrole, 2-butylpyrrole, 3-methylpyrrole, 3-ethylpyrrole, 3-propylpyrrole, 3-butylpyrrole, 3-ethyl-2,4-dimethylpyrrole, 2,3,4,5-tetramethylpyrrole, 2,3,4,5-tetraethylpyrrole, 2,2'-bipyridine, 1,8-Diazabicyclo[5.4.0]undec-7-ene, di(2-pyridyl)dimethylsilane, N,N,N',N'-tetramethylethylenediamine, 1,10-phenanthroline, 2,9-dimethyl-1,10-phenanthroline, glyoxal-bis(mesityl)-1,2-diimine and the like, including substituted derivatives thereof. Suitable amines can be primary amines, secondary amines, or tertiary amines.

Suitable phosphines and other phosphorus compounds can include, but are not limited to, trimethylphosphine, triethylphosphine, tripropylphosphine, tributylphosphine, phenylphosphine, tolylphosphine, diphenylphosphine, ditolylphosphine, triphenylphosphine, tritolylphosphine, methyldiphenylphosphine, dimethylphenylphosphine, ethyldiphenylphosphine, diethylphenylphosphine, tricyclohexylphosphine, trimethyl phosphite, triethyl phosphite, tripropyl phosphite, triisopropyl phosphite, tributyl phosphite and tricyclohexyl phosphite, 2-(di-t-butylphosphino)biphenyl, 2-di-t-butylphosphino-1,1'-binaphthyl, 2-(di-t-butylphosphino)-3,6-dimethoxy-2',4',6'-tri-i-propyl-1,1'-biphenyl, 2-di-t-butylphosphino-2'-methylbiphenyl, 2-(di-t-butylphosphinomethyl)pyridine, 2-di-t-butylphosphino-2',4',6'-tri-i-propyl-1,1'-biphenyl, 2-(dicyclohexylphosphino)biphenyl, (S)-(+)-(3,5-dioxa-4-phospha-cyclohepta[2,1-a;3,4-a']dinaphthalen-4-yl)dimethylamine, 2-(diphenylphosphino)-2'-methoxy-1,1'-binaphthyl, 1,2,3,4,5-pentaphenyl-1'-(di-t-butylphosphino)ferrocene, 2,2'-bis(diphenylpho sphino)-1,1'-binaphthyl (BINAP), 1,2-bis(dimethylphosphino)ethane, 1,2-bis(diethylphosphino)ethane, 1,2-bis(dipropylphosphino)-ethane, 1,2-bis(diisopropylphosphino)ethane, 1,2-bis(dibutyl-phosphino)ethane, 1,2-bis(di-t-butyl-phosphino)ethane, 1,2-bis(dicyclohexylphosphino)ethane, 1,3-bis(dicyclohexylphosphino)propane, 1,3-bis(diisopropylphosphino)propane, 1,3-bis(diphenylphosphino)propane, 1,3-bis(di-t-butylphosphino)propane, 1,4-bis(diisopropylphosphino)butane, 1,4-bis(diphenylphosphino)butane, 2,2'-bis[bis(3,5-dimethylphenyl)phosphino]-4,4',6,6'-tetramethoxybiphenyl, 2,6-bis(di-t-butylphosphinomethyl)pyridine, 2,2'-bis(dicyclohexylphosphino)-1,1'-biphenyl, bis(2-dicyclohexylphosphinophenyl)ether, 5,5'-bis(diphenylphosphino)-4,4'-bi-1,3-benzodioxole, 2-t-butylphosphinomethylpyridine, bis(diphenylphosphino)ferrocene, bis(diphenylphosphino)methane, bis(dicyclohexylphosphino)methane, bis(di-t-butylphosphino)methane, and the like, including substituted derivatives thereof.

In other aspects, the ligand used to form the metalalactone or the transition metal precursor compound can be a carbene, for example, a N-heterocyclic carbene (NHC) compound. Representative and non-limiting examples of suitable N-heterocyclic carbene (NHC) materials include the following:

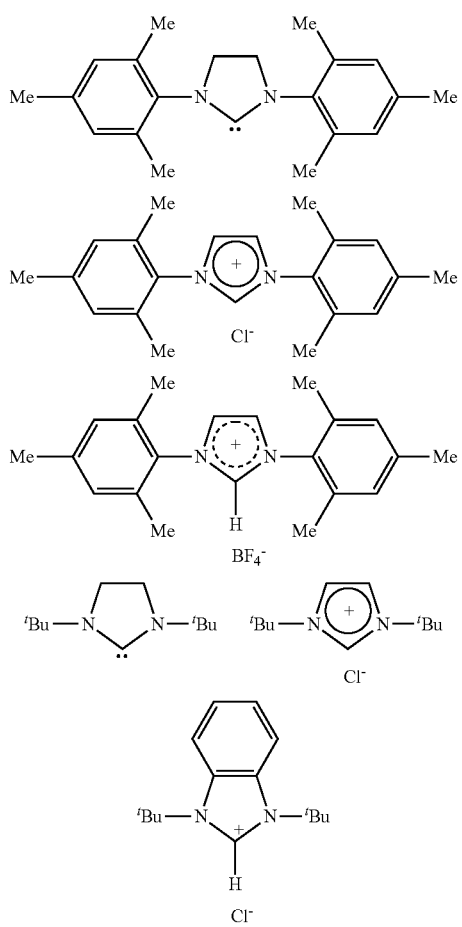

Illustrative and non-limiting examples of metalalactone complexes (representative nickelalactones) suitable for use as described herein include the following compounds (Cy=cyclohexyl, ᵗBu=tert-butyl):

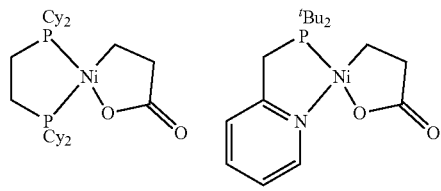

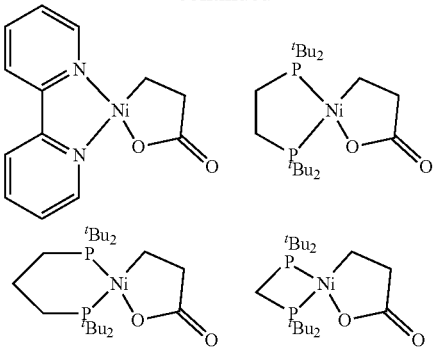

The transition metal precursor compounds corresponding to these illustrative metalalactones are shown below:

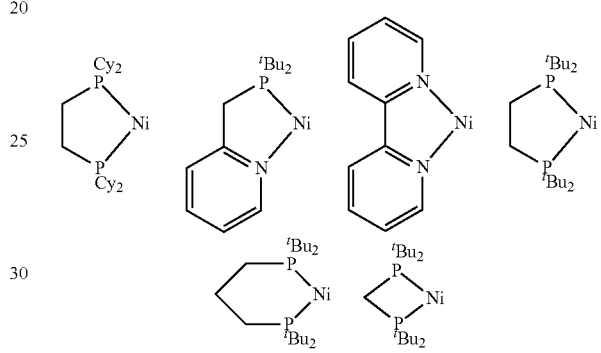

Metalalactones can be synthesized according to the following general reaction scheme shown in Scheme 2, which is illustrated with nickel as the transition metal ($Ni(COD)_2$ is bis(1,5-cyclooctadiene) nickel(0)), and according to suitable procedures well known to those of skill in the art.

Scheme 2

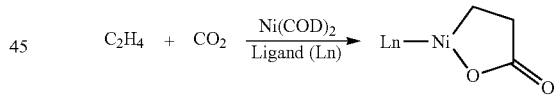

Suitable ligands, transition metal precursor compounds, and metalalactones are not limited solely to those ligands, transition metal precursor compounds, and metalalactones disclosed herein. Other suitable ligands, transition metal precursor compounds, and metalalactones are described, for example, in U.S. Pat. Nos. 7,250,510, 8,642,803, and 8,697,909; Journal of Organometallic Chemistry, 1983, 251, C51-053; Z. Anorg. Allg. Chem., 1989, 577, 111-114; Journal of Organometallic Chemistry, 2004, 689, 2952-2962; Organometallics, 2004, Vol. 23, 5252-5259; Chem. Commun., 2006, 2510-2512; Organometallics, 2010, Vol. 29, 2199-2202; Chem. Eur. J., 2012, 18, 14017-14025; Organometallics, 2013, 32 (7), 2152-2159; and Chem. Eur. J., 2014, Vol. 20, 11, 3205-3211; the disclosures of which are incorporated herein by reference in their entirety.

The following references provide information related to the structure and/or activity relationships in the olefin and $CO_2$ coupling process, as observed by changes in phenoxide structure, the phosphine ligand structure, and other ligand structures: Manzini, S.; Huguet, N.; Trapp, O.; Schaub, T. Eur. J. Org. Chem. 2015, 7122; and Al-Ghamdi, M.; Vummaleti, S. V. C.; Falivene, L.; Pasha, F. A.; Beetstra, D. J.; Cavallo, L. Organometallics 2017, 36, 1107-1112. These references are incorporated herein by reference in their entireties.

Generally, the features of the processes disclosed herein (e.g., the metalalactone, the diluent, the CMSO and MT-CMSO, the α,β-unsaturated carboxylic acid or the salt thereof, the transition metal precursor compound, the olefin, and the reaction conditions under which the α,β-unsaturated carboxylic acid, or a salt thereof, is formed, among others) are independently described, and these features can be combined in any combination to further describe the disclosed processes.

Process Steps and Conditions

In accordance with an aspect of the present disclosure, a process for performing a metalalactone elimination reaction is disclosed, in which the process forms an α,β-unsaturated carboxylic acid or a salt thereof. This process can comprise (or consist essentially of, or consist of):
  a) contacting
    i) a metalalactone compound;
    ii) a diluent; and
    iii) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
  b) subjecting the reaction mixture to reaction conditions suitable to form the α,β-unsaturated carboxylic acid or the salt thereof.

For example, the suitable reaction conditions may induce a metalalactone elimination reaction to produce the α,β-unsaturated carboxylic acid or a salt thereof. In this aspect, the metalalactone can be present in the reaction mixture at a concentration of less than 0.2 mM (millimolar).

Suitable metalalactones, diluents, CMSO and MT-CMSO, sulfur oxoacid anion-modified solid oxides, a phosphorus oxoacid anion-modified solid oxides, and a halide ion-modified solid oxides are disclosed hereinabove. In this process for forming the α,β-unsaturated carboxylic acid or the salt thereof, for instance, at least a portion of the diluent can comprise the α,β-unsaturated carboxylic acid, or the salt thereof, that is formed in step b) of this process.

In accordance with another aspect of the present disclosure, a process for producing an α,β-unsaturated carboxylic acid, or a salt thereof, is disclosed. This process can comprise (or consist essentially of, or consist of):
  a) contacting in any order
    i) a transition metal precursor compound comprising at least one first ligand;
    ii) optionally, at least one second ligand;
    iii) an olefin;
    iv) carbon dioxide ($CO_2$);
    v) a diluent; and
    vi) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
  b) subjecting the reaction mixture to reaction conditions suitable to form the α,β-unsaturated carboxylic acid or the salt thereof.

Similarly, the suitable reaction conditions may induce a metalalactone elimination reaction to produce the α,β-unsaturated carboxylic acid or a salt thereof. In this aspect, the metalalactone can be present in the reaction mixture at a concentration of less than 0.2 mM (millimolar).

In accordance with an aspect of the present disclosure, a process for performing a metalalactone elimination reaction is disclosed, in which the process forms an α,β-unsaturated carboxylic acid or a salt thereof. This process can comprise (or consist essentially of, or consist of):
  a) contacting
    i) a metalalactone compound comprising a Group 8-10 metal;
    ii) a diluent; and
    iii) a sulfur oxoacid anion-modified solid oxide or a halide ion-modified solid oxide that has been treated with [1] a sodium base, or [2] a sodium salt and an acid, to provide a reaction mixture; and
  b) subjecting the reaction mixture to reaction conditions suitable to induce a metalalactone elimination reaction to form the α,β-unsaturated carboxylic acid or the salt thereof.

In an aspect of this disclosure, a process for forming an α,β-unsaturated carboxylic acid or a salt thereof is provided, in which the process can comprise (or consist essentially of, or consist of):
  a) contacting in any order
    i) a group 8-11 transition metal precursor;
    ii) an olefin;
    iii) carbon dioxide ($CO_2$);
    iv) a diluent; and
    v) a sulfur oxoacid anion-modified solid oxide or a halide ion-modified solid oxide that has been treated with [1] a sodium base, or [2] a sodium salt and an acid, to provide a reaction mixture; and
  b) subjecting the reaction mixture to reaction conditions suitable to produce the α,β-unsaturated carboxylic acid or the salt thereof.

In one further aspect, there is provided a process for forming an α,β-unsaturated carboxylic acid or a salt thereof is provided, in which the process can comprise comprise (or consist essentially of, or consist of):
  a) contacting in any order
    i) a group 8-11 transition metal catalyst;
    ii) an olefin;
    iii) carbon dioxide ($CO_2$);
    iv) a diluent; and
    v) a sulfur oxoacid anion-modified solid oxide, a phosphorus oxoacid anion-modified solid oxide, or a halide ion-modified solid oxide that has been treated with [1] a sodium base, or [2] a sodium salt and an acid, to provide a reaction mixture; and
  b) contacting the reaction mixture with [1] an alkali metal-containing base selected from an alkali metal or an alkaline earth metal oxide, hydroxide, alkoxide, aryloxide, amide, alkyl amide, arylamide, or carbonate, or [2] an alkali metal salt and an acid to produce an α,β-unsaturated carboxylic acid salt;
  wherein the contacting step is carried out in the absence of a non-nucleophilic base.

In these processes for producing an α,β-unsaturated carboxylic acid or a salt thereof, for instance, at least a portion of the diluent of the reaction mixture comprising the adduct of the metalalactone can be removed after step a), and before step b), of this process. Suitable elements of each of these aspects of the disclosure are provided hereinabove.

As discussed further in this disclosure, the above processes can further comprise a step of contacting a transition metal precursor compound comprising at least one first ligand, an olefin, and carbon dioxide ($CO_2$) to form the metalalactone comprising at least one ligand. That is, at least one ligand of the transition metal precursor compound can be carried over to the metalalactone. In further aspects, the above processes can further comprise a step of contacting a transition metal precursor compound comprising at least one first ligand with at least one second ligand, an olefin, and carbon dioxide ($CO_2$) to form the metalalactone comprising at least one ligand. In this aspect, the ligand set of the metalalactone typically comprises the at least one second ligand. That is, the metalalactone ligand can comprise the at least one first ligand, the at least one second ligand, or a combination thereof.

In some aspects, the contacting step, step a) of the above processes, can include contacting, in any order, the metalalactone, the diluent, and the MT-CMSO as set out above, and additional unrecited materials. In other aspects, the contacting step can consist essentially of, or consist of, the metalalactone, the diluent, and the MT-CMSO components. Likewise, additional materials or features can be employed in the applying reaction conditions step, step b) of the above processes, that forms or produces the α,β-unsaturated carboxylic acid, or the salt thereof. Further, it is contemplated that these processes for producing an α,β-unsaturated carboxylic acid or a salt thereof by a metalalactone elimination reaction can employ more than one metalalactone and/or more than one MT-CMSO. Additionally, a mixture or combination of two or more diluents can be employed.

Any suitable reactor, vessel, or container can be used to contact the metalalactone, diluent, and MT-CMSO, non-limiting examples of which can include a flow reactor, a continuous reactor, a fixed bed reactor, a moving reactor bed, a stirred bed reactor, a bubbling bed reactor, and a stirred tank reactor, including more than one reactor in series or in parallel, and including any combination of reactor types and arrangements. In particular aspects consistent with this disclosure, the metalalactone and the diluent can contact a fixed bed of the MT-CMSO, for instance, in a suitable vessel, such as in a continuous fixed bed reactor. In other aspects, consistent with this disclosure, the metalalactone and the diluent can contact a moving bed of the MT-CMSO, for instance, in a suitable vessel, such as in a moving reactor bed, a stirred bed reactor, or a bubbling bed reactor. In further aspects, combinations of more than one MT-CMSO can be used, such as a mixed bed of a first MT-CMSO and a second MT-CMSO, or sequential beds of a first MT-CMSO and a second MT-CMSO. In still further aspects, the MT-CMSO of the contacting step a) is arranged as a fixed bed, a bubbling bed, a moving bed, or a stirred bed. In these and other aspects, the feed stream can flow upward or downward through the fixed bed. For instance, the metalalactone and the diluent can contact the first MT-CMSO and then the second MT-CMSO in a downward flow orientation, and the reverse in an upward flow orientation. In a different aspect, the metalalactone and the MT-CMSO can be contacted by mixing or stirring in the diluent, for instance, in a suitable vessel, such as a stirred tank reactor.

Step a) of the process for producing an α,β-unsaturated carboxylic acid or a salt thereof also recites forming an adduct of the metalalactone and the MT-CMSO wherein the MT-CMSO comprises associated metal cations. Without intending to be bound by theory, there is some interaction between the metalalactone and the MT-CMSO and its associated metal cations that are believed to destabilize the metalalactone for its elimination of the metal acrylate. This interaction can be referred to generally as an adduct of the metalalactone and MT-CMSO or an adduct of the α,β-unsaturated carboxylic acid with the MT-CMSO. This adduct can contain all or a portion of the α,β-unsaturated carboxylic acid and can be inclusive of salts of the α,β-unsaturated carboxylic acid.

Accordingly, applying reaction conditions to the reaction mixture suitable to form an α,β-unsaturated carboxylic acid or a salt thereof is intended to reflect any concomitant or subsequent conditions to step a) of the above processes that release the α,β-unsaturated carboxylic acid or a salt thereof from the adduct, regardless of the specific nature of the adduct.

For example, in step b) of the process of applying reaction conditions to the reaction mixture suitable to form an α,β-unsaturated carboxylic acid or a salt thereof, the adduct of the metalalactone and the MT-CMSO and its associated metal cations as defined herein is subjected to some chemical or other conditions or treatment to produce the α,β-unsaturated carboxylic acid or its salt. Various methods can be used to liberate the α,β-unsaturated carboxylic acid or its salt, from the MT-CMSO. In one aspect, for instance, the treating step can comprise contacting the adduct of the metalalactone and the MT-CMSO and its associated metal cations with an acid. Representative and non-limiting examples of suitable acids can include HCl, acetic acid, and the like, as well as combinations thereof. In another aspect, the treating step can comprise contacting the adduct of the metalalactone and the MT-CMSO and its associated metal cations with a base. Representative and non-limiting examples of suitable bases can include carbonates (e.g., $Na_2CO_3$, $Cs_2CO_3$, $MgCO_3$), hydroxides (e.g., $Mg(OH)_2$, $Na(OH)$, alkoxides (e.g., $Al(O^iPr)_3$, $Na(O^tBu)$, $Mg(OEt)_2$), and the like, as well as combinations thereof ($^iPr$=isopropyl, $^tBu$=tert-butyl, Et=ethyl). In yet another aspect, the treating step can comprise contacting the adduct of the metalalactone and the MT-CMSO and its associated metal cations with a suitable solvent. Representative and non-limiting examples of suitable solvents can include carbonyl-containing solvents such as ketones, esters, amides, etc. (e.g., acetone, ethyl acetate, N,N-dimethylformamide, etc., as described herein above), alcohol solvents, water, and the like, as well as combinations thereof.

In still another aspect, the treating step can comprise heating the adduct of the metalalactone and the MT-CMSO and its associated metal cations to any suitable temperature. This temperature can be in a range, for example, from 50° C. to 1000° C., from 100° C. to 800° C., from 150° C. to 600° C., from 250° C. to 1000° C., from 250° C. to 550° C., or from 150° C. to 500° C. The duration of this heating step is not limited to any particular period of time, as long of the period of time is sufficient to liberate the α,β-unsaturated carboxylic acid from the MT-CMSO. As those of skill in the art recognize, the appropriate treating step depends upon several factors, such as the particular diluent used in the process, and the particular MT-CMSO used in the process, amongst other considerations. One further treatment step can comprise, for example, a workup step with additional olefin to displace an alkene-nickel bound acrylate.

In these processes for performing a metalalactone elimination reaction and for producing an α,β-unsaturated carboxylic acid (or a salt thereof), additional process steps can be conducted before, during, and/or after any of the steps described herein. As an example, these processes can further comprise a step (e.g., prior to step a)) of contacting a transition metal precursor compound with an olefin and carbon dioxide to form the metalalactone. Transition metal precursor compound are described hereinabove. Illustrative and non-limiting examples of suitable olefins can include ethylene, propylene, butene (e.g., 1-butene), pentene, hexene (e.g., 1-hexene), heptane, octene (e.g., 1-octene), and styrene and the like, as well as combinations thereof.

In aspects of this process that utilizes a transition metal precursor compound comprising at least one first ligand, the olefin can be ethylene, and the step of contacting a transition metal precursor compound with an olefin and carbon dioxide ($CO_2$) can be conducted using any suitable pressure of ethylene, or any pressure of ethylene disclosed herein, e.g., from 10 psig (70 KPa) to 1,000 psig (6,895 KPa), from 25 psig (172 KPa) to 500 psig (3,447 KPa), or from 50 psig (345 KPa) to 300 psig (2,068 KPa), and the like. Further, the olefin can be ethylene, and the step of contacting a transition metal precursor compound with an olefin and carbon dioxide ($CO_2$) can be conducted using a constant addition of the olefin, a constant addition of carbon dioxide, or a constant addition of both the olefin and carbon dioxide, to provide the reaction mixture. By way of example, in a process wherein the ethylene and carbon dioxide ($CO_2$) are constantly added, the process can utilize an ethylene:$CO_2$ molar ratio of from 5:1 to 1:5, from 3:1 to 1:3, from 2:1 to 1:2, or about 1:1, to provide the reaction mixture.

According to a further aspect of the above process that utilizes a transition metal precursor compound, the process can include the step of contacting a transition metal precursor compound with an olefin and carbon dioxide ($CO_2$) conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), and the like. In any of the processes disclosed herein, the processes can further comprise a step of monitoring the concentration of at least one reaction mixture component, at least one elimination reaction product, or a combination thereof, for any reason, such as to adjust process parameters in real time, to determine extent or reaction, or to stop the reaction at the desired point.

As illustrated, this process that utilizes a transition metal precursor compound comprising at least one first ligand includes one aspect in which no second ligand is employed in the contacting step, and another aspect in which a second ligand is used in the contacting step. That is, one aspect involves the contacting step of the process comprising contacting the transition metal precursor compound comprising at least one first ligand with the at least one second ligand. The order of contacting can be varied. For example, the contacting step of the process disclosed above can comprise contacting 1) the transition metal precursor compound comprising at least one first ligand with 2) the at least one second ligand to form a pre-contacted mixture, followed by contacting the pre-contacted mixture with the remaining components 3)-6) in any order to provide the reaction mixture.

Further embodiments related to the order of contacting, for example, the contacting step can include or comprise contacting the metalalactone, the diluent, and the MT-CMSO in any order. The contacting step can also comprise contacting the metalalactone and the diluent to form a first mixture, followed by contacting the first mixture with the MT-CMSO to form the reaction mixture. In a further aspect, the contacting step can comprise contacting the diluent and the MT-CMSO to form a first mixture, followed by contacting the first mixture with the metalalactone to form the reaction mixture. In yet a further aspect, the contacting step of the process further comprises contacting any number of additives, for example, additives that can be selected from an acid, a base, or a reductant.

Suitable transition metal precursors, first ligands, second ligands, olefins, diluents, MT-CMSOs with the associated metal cations are disclosed hereinabove. In some aspects, the contacting step—step a)—of this process can include contacting, in any order, the transition metal-ligand, the olefin, the diluent, the MT-CMSO, and carbon dioxide, and additional unrecited materials. In other aspects, the contacting step can consist essentially of, or consist of, contacting, in any order, the transition metal-ligand, the olefin, the diluent, the MT-CMSO, and carbon dioxide. Likewise, additional materials or features can be employed in the forming step of step b) of this process. Further, it is contemplated that this processes for producing an α,β-unsaturated carboxylic acid, or a salt thereof, can employ more than one transition metal-ligand complex and/or more than one MT-CMSO if desired and/or more than one olefin. Additionally, a mixture or combination of two or more diluents can be employed.

As above, any suitable reactor, vessel, or container can be used to contact the transition metal precursors, first ligands, second ligands, olefin, diluent, MT-CMSO, and carbon dioxide, whether using a fixed bed of the MT-CMSO, a stirred tank for contacting (or mixing), or some other reactor configuration and process. While not wishing to be bound by the following theory, a proposed and illustrative reaction scheme for this process is provided below as Scheme 3.

Scheme 3

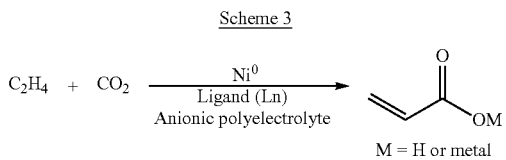

M = H or metal

Independently, the contacting and forming steps of any of the processes disclosed herein (i.e., for performing a metalalactone elimination reaction, for producing an α,β-unsaturated carboxylic acid, or a salt thereof), can be conducted at a variety of temperatures, pressures, and time periods. For instance, the temperature at which the components in step a) are initially contacted can be the same as, or different from, the temperature at which the forming step b) is performed. As an illustrative example, in the contacting step, the components can be contacted initially at temperature T1 and, after this initial combining, the temperature can be increased to a temperature T2 for the forming step (e.g., to form the α,β-unsaturated carboxylic acid, or the salt thereof). Likewise, the pressure can be different in the contacting step and the forming step. Often, the time period in the contacting step can be referred to as the contact time, while the time period in forming step can be referred to as the reaction time. The contact time and the reaction time can be, and often are, different.

In an aspect, the contacting step and/or the forming step of the processes disclosed herein can be conducted at a temperature in a range from 0° C. to 250° C.; alternatively, from 20° C. to 200° C.; alternatively, from 0° C. to 95° C.; alternatively, from 10° C. to 75° C.; alternatively, from 10° C. to 50° C.; or alternatively, from 15° C. to 70° C. In these and other aspects, after the initial contacting, the temperature can be changed, if desired, to another temperature for the forming step. These temperature ranges also are meant to encompass circumstances where the contacting step and/or the forming step can be conducted at a series of different temperatures, instead of at a single fixed temperature, falling within the respective ranges.

In an aspect, the contacting step and/or the forming step of the processes disclosed herein can be conducted at a pressure in a range from 5 (34 KPa) to 10,000 psig (68,948 KPa), such as, for example, from 5 psig (34 KPa) to 2500 psig (17,237 KPa). In some aspects, the pressure can be in a range from 5 psig (34 KPa) to 500 psig (3,447 KPa); alternatively, from 25 psig (172 KPa) to 3000 psig (20,684 KPa); alternatively, from 45 psig (310 KPa) to 1000 psig (6,895 KPa); or alternatively, from 50 psig (345 KPa) to 250 psig (1,724 KPa).

In another aspect, the processes disclosed herein can be conducted at a transition metal (catalyst) concentration of less than about 0.2 mM. Although the reaction works at higher concentrations, it has been discovered that at catalyst concentrations of less than about 0.2 mM, the acrylate yield (and turnover number) increase relative to the acrylate yield and turnover number of the 0.2 mM concentration processes, when conducted under otherwise similar or identical conditions. For example, the metalalactone or the transition metal precursor compound can be present in the reaction mixture at a concentration of less than about 0.18 mM (millimolar), less than about 0.15 mM, less than about 0.10 mM, less than about 0.05 mM, less than about 0.02 mM, less than about 0.015 mM, less than about 0.010 mM, less than about 0.005 mM, or less than about 0.002 mM. In these processes, the lower end of the catalyst concentration can be about 0.0001 mM, about 0.0002 mM, about 0.0005 mM, or about 0.001 mM.

The contacting step of the processes is not limited to any particular duration of time. That is, the respective components can be initially contacted rapidly, or over a longer period of time, before commencing the forming step. Hence, the contacting step can be conducted, for example, in a time period ranging from as little as 1-30 seconds to as long as 1-12 hours, or more. In non-continuous or batch operations, the appropriate reaction time for the forming step can depend upon, for example, the reaction temperature, the reaction pressure, and the ratios of the respective components in the contacting step, among other variables. Generally, however, the forming step can occur over a time period that can be in a range from 1 minute to 96 hours, such as, for example, from 2 minutes to 96 hours, from 5 minutes to 72 hours, from 10 minutes to 72 hours, or from 15 minutes to 48 hours.

If the process employed is a continuous process, then the metalalactone/MT-CMSO and catalyst contact/reaction time (or the transition metal precursors, first ligands, second ligands, olefin, diluent, MT-CMSO, and carbon dioxide contact/reaction time) can be expressed in terms of weight hourly space velocity (WHSV)—the ratio of the weight of the metalalactone (or the solution continuing the transition metal precursors, first ligands, second ligands, olefin, diluent, MT-CMSO, and carbon dioxide) which comes in contact with a given weight of MT-CMSO per unit time (for example, $hr^{-1}$). While not limited thereto, the WHSV employed, based on the amount of the MT-CMSO, can be in a range from 0.05 to 100 $hr^{-1}$, from 0.05 to 50 $hr^{-1}$, from 0.075 to 50 $hr^{-1}$, from 0.1 to 25 $hr^{-1}$, from 0.5 to 10 $hr^{-1}$, from 1 to 25 $hr^{-1}$, or from 1 to 5 $hr^{-1}$.

In the processes disclosed herein, the molar yield of the $\alpha,\beta$-unsaturated carboxylic acid, or the salt thereof), based on the metalalactone (or the metal precursors) is at least 2%, and more often can be at least 5%, at least 10%, or at least 15%. In particular aspects of this disclosure, the molar yield can be at least 18%, at least 20%, at least 25%, at least 35%, at least 50%, at least 60%, at least 75%, or at least 85%, or at least 90%, or at least 95%, or at least 100%. That is, catalytic formation of the $\alpha,\beta$-unsaturated carboxylic acid or the salt thereof can be effected with the disclosed system. For example, the molar yield of the $\alpha,\beta$-unsaturated carboxylic acid, or the salt thereof, based on the metalalactone or based on the transition metal precursor compound can be at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, or at least 500%.

The specific $\alpha,\beta$-unsaturated carboxylic acid (or salt thereof) that can be formed or produced using the processes of this disclosure is not particularly limited. Illustrative and non-limiting examples of the $\alpha,\beta$-unsaturated carboxylic acid can include acrylic acid, methacrylic acid, 2-ethylacrylic acid, cinnamic acid, and the like, as well as combinations thereof. Illustrative and non-limiting examples of the salt of the $\alpha,\beta$-unsaturated carboxylic acid can include sodium acrylate, potassium acrylate, magnesium acrylate, sodium (meth)acrylate, and the like, as well as combinations thereof.

Once formed, the $\alpha,\beta$-unsaturated carboxylic acid (or the salt thereof) can be purified and/or isolated and/or separated using suitable techniques which can include, but are not limited to, evaporation, distillation, chromatography, crystallization, extraction, washing, decanting, filtering, drying, and the like, including combinations of more than one of these techniques. In an aspect, the process can for performing a metalalactone elimination reaction (or the process for producing an $\alpha,\beta$-unsaturated carboxylic acid, or a salt thereof) can further comprise a step of separating or isolating the $\alpha,\beta$-unsaturated carboxylic acid (or the salt thereof) from other components, e.g., the diluent, the MT-CMSO, and the like.

EXAMPLES

The invention is further illustrated by the following examples, which are not to be construed in any way as imposing limitations upon the scope of this invention. Various other aspects, embodiments, modifications, and equivalents thereof which, after reading the description herein, can suggest themselves to one of ordinary skill in the art without departing from the spirit of the present invention or the scope of the appended claims.

A. General Considerations

Unless otherwise noted, all operations were performed under purified nitrogen or vacuum using standard Schlenk or glovebox techniques. Toluene (Honeywell) and was degassed and dried over activated 4 Å molecular sieves under nitrogen. Sodium tert-butoxide (NaO-t-Bu) and Amberlyst 36® H+ form were purchased from Sigma-Aldrich and used as received. Sodium chloride and sodium sulfate were purchased from Thermo-Fisher and used as received. Bis(1,5-cyclooctadiene)nickel(0) and 1,2-Bis(dicyclohexylphosphino)ethane were purchased from Strem Chemicals and used as received.

B. Preparation of Various Activators

Abbreviations. Throughout this disclosure, the following abbreviations are used. The abbreviation SSA refers to a "solid super acid", which may also be referred to as a "chemically-modified solid oxide" or CMSO, and which is prepared from a solid oxide such as alumina, silica, or silica-alumina, which has been chemically treated or modified with an electron-withdrawing anion such as sulfate, phosphate fluoride, or chloride. The specific SSA abbreviated S-SSA is sulfated alumina, and the specific SSA abbreviated M-SSA is fluorided silica-coated alumina. According to this disclosure, the SSA is metal-treated using, for example, sodium tert-butoxide (NaO-t-Bu) or potassium tert-butoxide (KO$^t$Bu) to form the metal-treated activators described herein. The abbreviations MT-SSA and MT-CMSO are used interchangeably to refer to the metal-treated solid super acid, also termed the metal-treated chemically-modified solid oxide. Representative preparations of some of the metal-treated chemically-modified solid oxides are disclosed in U.S. Pat. No. 9,725,393, which is incorporated herein in its entirety.

Sulfated Alumina (S-SSA). Alumina was mixed with a solution of sulfuric acid in methanol, to result in approximately 15 wt. % (weight percent) sulfate based on the weight of the sulfated alumina. After drying under vacuum at 110° C. overnight, the dried powder was calcined at 600° C. in dry air for three hours. After being allowed to cool to ambient temperature, the resulting sulfated alumina (S-SSA) was used to prepare the metal-treated sulfated alumina.

Fluorided Silica-Coated Alumina (M-SSA). The fluorided silica-coated alumina SSA was prepared by first contacting alumina with tetraethylorthosilicate in isopropanol to equal 25 wt. % $SiO_2$. After drying, the silica-coated alumina was calcined at 600° C. for 3 hours, and then allowed to cool to ambient temperature. The fluorided silica-coated alumina (7 wt. % F) was prepared by impregnating the calcined silica-coated alumina with an ammonium bifluoride solution in methanol, drying the resulting solid, and then calcining at 600° C. for 3 hours. After being allowed to cool to ambient temperature, the resulting fluorided silica-coated alumina (M-SSA) was used to prepare the metal-treated fluorided silica-coated alumina.

Sodium-Treated Sulfated Alumina (NaO-t-Bu on S-SSA). The sulfated alumina prepared as above (4.2 g) and sodium tert-butoxide (2 g) were combined in 60 mL of toluene, forming a yellow suspension. This mixture was stirred at ambient temperature for 18 hours, the solid was filtered off and washed with 10 mL of toluene, forming the colorless solid of sodium-treated sulfated alumina.

Sodium-Treated Fluorided Silica-Coated Alumina (NaO-t-Bu on M-SSA). Fluorided silica-coated alumina (5 g) and sodium tert-butoxide (2 g) were combined in 60 mL of toluene forming a yellow suspension. The mixture was stirred at ambient temperature for 18 hours, the solid was filtered off and washed with 10 mL of toluene, forming the colorless solid of filtered and washed with 10 mL toluene forming a colorless solid of sodium-treated fluorided silica-coated alumina.

Sodium-Treated Sulfated Alumina using a Sodium Salt and an Acid (NaCl/$H_2SO_4$/S-SSA). A metal-treated sulfated alumina (S-SSA), specifically sodium-treated sulfated alumina, can be prepared by the alternative method of treating the S-SSA with the combination of a sodium-containing salt and an acid, as follows. Sulfated alumina (2.5 g) prepared as described above was taken up in 25 mL of water followed by 1 mL of concentrated sulfuric acid. The suspension was left to stir for 30-60 minutes, after which a saturated brine (NaCl) solution (25 mL) was added. After stirring this mixture overnight, the resulting suspension was filtered off, and the collected solid was washed with DI (deionized) water (3×100 mL). The washed solid was dried under vacuum at 60° C. for about 5 hours.

Sodium-Treated Amberlyst 36® (NaCl-Amberlyst 36®). Amberlyst 36® H+ form (2.5 g) was added to 50 mL of an aqueous sodium chloride solution (2.0 M) and was stirred overnight at room temperature. The resulting solid was filtered off, washed with water (3×50 mL), and vacuum-dried at 60° C.

C. Experimental Procedure for Ethylene/Carbon Dioxide Coupling

A 1-liter autoclave pressure reactor was charged with 500 mL of toluene solvent, followed by a combined mixture of Ni(COD)$_2$ (0.10 mmol, for 0.2 millimolar (mM) solution), bis(dicyclohexylphosphino)ethane (0.11 mole equivalent relative to Ni), and the solid activator (sodium-treated chemically-modified solid oxide) shown in the following table and prepared as above (1.00 g). The nickel concentration was adjusted to form the 0.02 mM and 0.002 mM solutions in the Examples set out in the following table.

The reactor was heated to 50° C. and pressurized with 150 psig of ethylene and equilibrated for 5-10 minutes, then pressurized and equilibrated with carbon dioxide. The reactor was then heated to 100° C. and stirred for 6 hours. After this time, the reactor was allowed to cool to ambient temperature, the reactor was slowly vented, and the resulting mixture was collected. The solvent was removed in vacuo and the residue was stirred in 10-20 mL of deuterium oxide ($D_2O$) for 30 min prior to the addition of a sorbic acid/acetone-$d_6$ solution. This mixture was filtered and analyzed via NMR with sorbic acid as the internal standard for acrylate yield determination.

D. Conversion of Carbon Dioxide and Ethylene to Sodium Acrylate with Various Activators The following table summarizes the results of the converting carbon dioxide and ethylene to sodium acrylate with the various metal-treated chemically-modified solid oxide activators described in this disclosure. This reaction is summarized in Equation 1, where the solid activator is the MT-CMSO as disclosed herein.

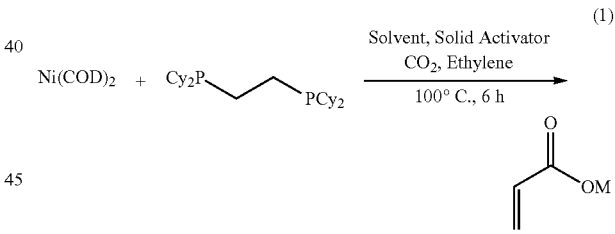

TABLE 1

Summary of conversion of carbon dioxide and ethylene to sodium acrylate using the MT-CMSO described herein.$^A$

| Example | Activator | Nickel Concentration [Ni], mM | Acrylate Yield (%) |
|---|---|---|---|
| Sodium-Treated Sulfated Alumina | | | |
| 1 | NaO-t-Bu-(S-SSA) | 0.2 | 218 |
| 2 | NaO-t-Bu-(S-SSA) | 0.02 | 1236 |
| 3 | NaCl/$H_2SO_4$-(S-SSA) | 0.02 | 131 |
| Sodium Sulfate | | | |
| 4 | Na$_2$SO$_4$ (commercial) | 0.02 | 42 |
| Sodium-Treated Fluorided Silica-Coated Alumina | | | |
| 5 | NaO-t-Bu-(M-SSA) | 0.2 | 158 |
| 6 | NaO-t-Bu-(M-SSA) | 0.02 | 250 |
| 7 | NaO-t-Bu-(M-SSA) | 0.002 | 561 |

TABLE 1-continued

Summary of conversion of carbon dioxide and ethylene to sodium acrylate using the MT-CMSO described herein.[A]

| Example | Activator | Nickel Concentration [Ni], mM | Acrylate Yield (%) |
|---|---|---|---|
| | Sodium-Treated Amberlyst 36 ® | | |
| 8 | NaCl-Amberlyst 36 ® | 0.2 | 3.7 |
| 9 | NaCl-Amberlyst 36 ® | 0.02 | 18 |

[A]Reaction conditions: 1.1 mole equivalent diphosphine ligand, 500 mL of solvent (toluene), 1.0 g solid activator (MT-CTSO); reactor equilibrated to 150 psi ethylene followed by 300 psi carbon dioxide prior to heating.

The Table 1 data shows that the sulfate moiety used in the sulfated alumina of Examples 1-3 enhances the turnover rate as a function of lower concentrations of the nickel catalyst. The fluoride silica-coated alumina (or mullite, M-SSA) exhibits a similar behavior, but the catalyst concentration is diluted even further than in the sulfated alumina for the effect to be considerable. A control run employing commercially available sodium sulfate also yielded the acrylate product in 42% yield. To further probe the concentration effect, crosslinked polystyrene sulfonate (Amberlite 36®) which had been treated with brine (aqueous NaCl) showed a substantially increased yield when the nickel catalyst concentration was decreased to 10% of its initial 0.2 mM concentration.

While not intending to be bound by theory, it is possible that a loose sulfate-sodium interaction allows for a more facile transfer to the nickelalactone to subsequently destabilize it, ultimately affording the eliminated nickel-bound acrylate species. Again, while not bound by theory, it is possible that at the relatively higher catalyst concentrations, nickelalactone oligomers or other aggregate species may inhibit the sodium interaction necessary for elimination to the nickel-acrylate adduct. Further, and not being bound by theory, it is possible that at higher catalyst concentrations, cyclooctadiene (COD) binds more effectively to the nickel center and inhibits ethylene coordination. Experiments using in the absence of COD using a nickelalactone complex as the catalyst precursor resulted in lower acrylate yields, suggesting that COD may behave as a thermodynamically less stable placeholder for incoming ethylene/$CO_2$ molecules.

The invention is described above with reference to numerous aspects and embodiments, and specific examples. Many variations will suggest themselves to those skilled in the art in light of the above detailed description. All such obvious variations are within the full intended scope of the appended claims. Other aspects of the invention can include, but are not limited to, the following aspects. Many aspects are described as "comprising" certain components or steps, but alternatively, can "consist essentially of" or "consist of" those components or steps unless specifically stated otherwise.

ASPECTS OF THE DISCLOSURE

Aspect 1. A process for forming an α,β-unsaturated carboxylic acid or a salt thereof, the process comprising:
a) contacting
  i) a metalalactone compound;
  ii) a diluent; and
  iii) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
b) subjecting the reaction mixture to reaction conditions suitable to form the α,β-unsaturated carboxylic acid or the salt thereof;
wherein the metalalactone is present in the reaction mixture at a concentration of less than 0.2 mM (millimolar).

Aspect 2. A process according to aspect 1, wherein the reaction mixture comprises an adduct of the metalalactone and the metal-treated chemically-modified solid oxide.

Aspect 3. A process for forming an α,β-unsaturated carboxylic acid or a salt thereof, the process comprising:
a) contacting in any order
  i) a transition metal precursor compound comprising at least one first ligand;
  ii) optionally, at least one second ligand;
  iii) an olefin;
  iv) carbon dioxide ($CO_2$);
  v) a diluent; and
  vi) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
b) subjecting the reaction mixture to reaction conditions suitable to form the α,β-unsaturated carboxylic acid or the salt thereof;
wherein the transition metal precursor compound is present in the reaction mixture at a concentration of less than 0.2 mM (millimolar).

Aspect 4. A process according to aspect 3, wherein the reaction mixture comprises a metalalactone.

Aspect 5. A process according to aspect 4, wherein the reaction mixture comprises an adduct of the metalalactone and the metal-treated chemically-modified solid oxide.

Aspect 6. The process according to any one of aspects 1-5, wherein the metalalactone or the transition metal precursor compound is present in the reaction mixture at a concentration of less than 0.18 mM (millimolar), less than 0.15 mM, less than 0.10 mM, less than 0.05 mM, less than 0.02 mM, less than 0.015 mM, less than 0.010 mM, less than 0.005 mM, or less than 0.002 mM.

Aspect 7. The process according to any one of aspects 1-6, wherein the chemically-modified solid oxide comprises or is selected from a solid oxide that is chemically modified with an electron-withdrawing anion.

Aspect 8. The process according to any one of aspects 1-6, wherein the chemically-modified solid oxide is generated by treatment of a solid oxide with an acid or a salt of an electron-withdrawing anion.

Aspect 9. The process according to aspect 8, wherein, following treatment of the solid oxide with the acid or the salt of an electron-withdrawing anion, the chemically-modified solid oxide is dried and calcined.

Aspect 10. The process according to any one of aspects 1-6, wherein the chemically-modified solid oxide is produced by a process comprising contacting any suitable solid oxide and any suitable solid oxide with an electron-withdrawing anion to provide a mixture, and concurrently and/or subsequently drying and/or calcining the mixture.

Aspect 11. The process according to any one of aspects 1-10, wherein the solid oxide of the chemically-modified solid oxide comprises or is selected from $Al_2O_3$, $B_2O_3$, BeO, $Bi_2O_3$, CdO, $Co_3O_4$, $Cr_2O_3$, CuO, $Fe_2O_3$, $Ga_2O_3$, $La_2O_3$, $Mn_2O_3$, $MoO_3$, $Na_2O$, NiO, $P_2O_5$, $Sb_2O_5$, $SiO_2$, $SnO_2$, SrO, $ThO_2$, $TiO_2$, $V_2O_5$, $WO_3$, $Y_2O_3$, ZnO, $ZrO_2$, $K_2O$, CaO, $La_2O_3$, $Ce_2O_3$, mixtures thereof, mixed oxides thereof, and any combinations thereof.

Aspect 12. The process according to any one of aspects 1-10, wherein the chemically-modified solid oxide comprises a solid oxide comprising or selected from silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

Aspect 13. The process according to any one of aspects 1-12, wherein the chemically-modified solid oxide comprises a solid oxide that is chemically modified with an electron-withdrawing anion, and wherein the electron-withdrawing anion comprises or is selected from sulfate, bisulfate, fluoro sulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof.

Aspect 14. The process according to any one of aspects 1-12, wherein the chemically-modified solid oxide is generated by treatment of a solid oxide with sulfuric acid, sulfate ion, bisulfate ion, fluoro sulfuric acid, fluorosulfate ion, phosphoric acid, phosphate ion, fluorophosphoric acid, monofluorophosphate ion, triflic (trifluoromethanesulfonic) acid, triflate trifluoromethanesulfonate) ion, methanesulfonic acid, mesylate (methanesulfonate) ion, toluenesulfonic acid, tosylate (toluenesulfonate) ion, thiosulfate ion, $C_1$-$C_{10}$ alkyl sulfonic acid, $C_1$-$C_{10}$ alkyl sulfonate ion, $C_6$-$C_{14}$ aryl sulfonic acid, $C_6$-$C_{14}$ aryl sulfonate ion, fluoride ion, chloride ion, or any combination thereof.

Aspect 15. The process according to any one of aspects 1-12, wherein the chemically-modified solid oxide comprises a sulfated solid oxide, bisulfated (hydrogen sulfated) solid oxide, fluorosulfated solid oxide, phosphated solid oxide, fluorophosphated solid oxide, fluoride solid oxide, or chloride solid oxide.

Aspect 16. The process according to any one of aspects 1-12, wherein the chemically-modified solid oxide comprises a sulfated solid oxide or a phosphated solid oxide.

Aspect 17. The process according to any one of aspects 1-12, wherein the chemically-modified solid oxide comprises a sulfated solid oxide.

Aspect 18. The process according to any one of aspects 1-12, wherein the chemically-modified solid oxide comprises a solid oxide that is chemically modified with an electron-withdrawing anion, wherein:
a) the solid oxide comprises or is selected from silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof; and
b) the electron-withdrawing anion comprises or is selected from sulfate, bisulfate, fluorosulfate, phosphate, fluorophosphates, fluoride, or chloride.

Aspect 19. The process according to any one of aspects 1-12, wherein [a] the chemically-modified solid oxide comprises a solid oxide comprising or selected from alumina, silica-alumina, silica-coated alumina, or a mixture thereof, and [b] the electron-withdrawing anion comprises or is selected from sulfate, phosphate, or fluoride.

Aspect 20. The process according to any one of aspects 1-19, wherein the sulfur oxoacid anion-modified solid oxide is generated by sulfuric acid treatment or sulfate ion treatment.

Aspect 21. The process according to any one of aspects 1-19, wherein the phosphorus oxoacid anion-modified solid oxide is generated by phosphoric acid treatment or phosphate ion treatment.

Aspect 22. The process according to any one of aspects 1-21, wherein the metal-treated chemically-modified solid oxide is prepared by [a] contacting a solid oxide with a sulfur oxoacid anion, a phosphorus oxoacid anion, or a halide ion to provide the chemically-modified solid oxide, followed by [b] contacting the chemically-modified solid oxide with [1] a metal-containing base or [2] a metal-containing salt in combination with an acid.

Aspect 23. The process according to aspect 22, wherein the sulfur oxoacid anion is provided by sulfuric acid or a sulfate salt, the phosphorus oxoacid anion is provided by phosphoric acid or a phosphate salt, and the halide ion is provided by a hydrohalic acid or a halide salt.

Aspect 24. The process according to any one of aspects 1-23, wherein the metal-treated chemically-modified solid oxide comprises metal cations are selected from a Group 1, 2, 12 or 13 metal.

Aspect 25. The process according to any one of aspects 1-23, wherein the metal-treated chemically-modified solid oxide comprises any suitable Lewis acidic metal cation or any Lewis acidic metal cation disclosed herein.

Aspect 26. The process according to any one of aspects 1-23, wherein the metal-treated chemically-modified solid oxide comprises an alkali metal cation, an alkaline earth metal cation, or any combination thereof.

Aspect 27. The process according to any one of aspects 1-23, wherein the metal-treated chemically-modified solid oxide comprises cations selected from lithium, sodium, potassium, rubidium, cesium, magnesium, calcium, strontium, barium, copper, zinc, aluminum, or gallium.

Aspect 28. The process according to any one of aspects 1-23, wherein the metal-treated chemically-modified solid oxide comprises sodium ions or potassium ions.

Aspect 29. The process according to any one of aspects 1-23, wherein the metal-treated chemically-modified solid oxide is prepared by contacting the chemically-modified solid oxide with [a] a metal-containing base or [b] a metal-containing salt in combination with an acid.

Aspect 30. The process according to aspect 29, wherein, independently:
a) the metal-containing base comprises any suitable base or any base disclosed herein, e.g., carbonates (e.g., $Na_2CO_3$, $K_2CO_3$, $Cs_2CO_3$, $CaCO_3$, $MgCO_3$), hydroxides (e.g., NaOH, KOH, $Mg(OH)_2$), alkoxides (e.g., Na(O$^t$Bu), K(O$^t$Bu), Mg(OEt)$_2$, Al(O$^i$Pr)$_3$), aryloxides (e.g. Na(OC$_6$H$_5$), K(OC$_6$H$_5$), sulfates (e.g. $Na_2SO_4$, $K_2SO_4$, $CaSO_4$, $MgSO_4$), and phosphates (e.g. $Na_3PO_4$, $K_3PO_4$), etc.,
b) the metal-containing salt comprises any suitable metal-containing salt or any metal-containing salt disclosed herein, e.g. chlorides (e.g. NaCl, KCl, RbCl, $CaCl_2$, $MgCl_2$), bisulfates (e.g. $NaHSO_4$, $KHSO_4$, $Ca(HSO_4)_2$, $Mg(HSO_4)_2$), fluorosulfates (e.g. $NaSO_3F$, $KSO_3F$, $RbSO_3F$, $CsSO_3F$), hydrogen phosphates (e.g. $Na_2HPO_4$, $K_2HPO_4$), fluorophosphates (e.g. $Na_2PO_3F$, $K_2PO_3F$, $Cs_2PO_3F$, $CaPO_3F$, $MgPO_3F$), triflates (e.g $NaSO_3CF_3$, $KSO_3CF_3$), mesylates (e.g. $NaSO_3CH_3$, $KSO_3CH_3$), tosylates (e.g. $NaSO_3C_6H_4CH_3$, $KSO_3C_6H_4CH_3$), thiosulfates (e.g. $Na_2S_2O_3$, $K_2S_2O_3$), $C_1$-$C_{10}$ alkyl sulfonates (e.g. $NaSO_3R$, $KSO_3R$, wherein R is a $C_1$-$C_{10}$ alkyl), $C_6$-$C_{14}$ aryl sulfonates (e.g. $NaSO_3Ar$, $KSO_3Ar$, wherein Ar is a $C_6$-$C_{14}$ aryl), etc., and c) the acid comprises any suitable acid or any acid disclosed herein, e.g. sulfuric acid, hydrochloric acid, fluoro sulfuric acid, phosphoric acid, fluorophosphoric acid, triflic (trifluoromethanesulfonic) acid, methanesulfonic acid, toluenesulfonic acid, $C_1$-$C_{10}$ alkyl sulfonic acid, $C_6$-$C_{14}$ aryl sulfonic acid, etc., or any combination thereof.

Aspect 31. The process according to any one of aspects 1-30, wherein the metal-treated chemically-modified solid oxide is produced by a process comprising contacting any suitable chemically-modified solid oxide or any chemically-modified solid oxide disclosed herein and any suitable metal-containing compound or any metal-containing compound disclosed herein to provide a mixture, and concurrently and/or subsequently drying and/or calcining the mixture.

Aspect 32. The process according to any one of aspects 1-30, wherein the metal-treated chemically-modified solid oxide is produced by a process comprising contacting any suitable solid oxide with an electron-withdrawing anion to form a first mixture and concurrently and/or subsequently drying and/or calcining the first mixture, followed by contacting the dried and/or calcined first mixture with any suitable metal-containing compound to provide a second mixture, and concurrently and/or subsequently drying and/or calcining the second mixture.

Aspect 33. The process according to any one of aspects 1-30, wherein the metal-treated chemically-modified solid oxide is produced by a process comprising contacting any suitable solid oxide and any suitable electron-withdrawing anion and calcining (concurrently and/or subsequently) to form the chemically-modified solid oxide, and contacting the chemically-modified solid oxide with any suitable metal-containing compound.

Aspect 34. The process according to any one of aspects 1-30, wherein the metal-treated chemically-modified solid oxide comprises a chemically-modified solid oxide treated with an alkali metal, an alkaline earth metal, or any combination thereof in a total amount in a range from 1 to 30 wt. %, from 3 to 25 wt. %, or from 5 to 20 wt. %, based on the total weight of the metal-treated chemically-modified solid oxide.

Aspect 35. The process according to any one of aspects 1-34, wherein the diluent comprises any suitable non-protic solvent, or any non-protic solvent disclosed herein.

Aspect 36. The process according to any one of aspects 1-34, wherein the diluent comprises any suitable weakly coordinating or non-coordinating solvent, or any weakly coordinating or non-coordinating solvent disclosed herein.

Aspect 37. The process according to any one of aspects 1-34, wherein the diluent comprises any suitable aromatic hydrocarbon solvent, or any aromatic hydrocarbon solvent disclosed herein, e.g., benzene, xylene, toluene, etc.

Aspect 38. The process according to any one of aspects 1-34, wherein the diluent comprises any suitable ether solvent, or any ether solvent disclosed herein, e.g., THF, dimethyl ether, diethyl ether, dibutyl ether, etc.

Aspect 39. The process according to any one of aspects 1-34, wherein the diluent comprises any suitable carbonyl-containing solvent, or any carbonyl-containing solvent disclosed herein, e.g., ketones, esters, amides, etc. (e.g., acetone, ethyl acetate, N,N-dimethylformamide, etc.).

Aspect 40. The process according to any one of aspects 1-34, wherein the diluent comprises any suitable halogenated aromatic hydrocarbon solvent, or any halogenated aromatic hydrocarbon solvent disclosed herein, e.g., chlorobenzene, dichlorobenzene, etc.

Aspect 41. The process according to any one of aspects 1-34, wherein the diluent comprises THF, 2,5-$Me_2$THF, methanol, acetone, toluene, chlorobenzene, pyridine, or a combination thereof.

Aspect 42. The process according to any one of aspects 1-41, wherein the diluent comprises carbon dioxide.

Aspect 43. The process according to any one of aspects 1-42, wherein at least a portion of the diluent comprises the α,β-unsaturated carboxylic acid or the salt thereof, formed in the process.

Aspect 44. The process according to any one of aspects 1-43, wherein the contacting step comprises contacting the recited components in any order.

Aspect 45. The process according to any one of aspects 3-43, wherein the contacting step comprises contacting the transition metal precursor compound comprising at least one first ligand with the at least one second ligand.

Aspect 46. The process according to any one of aspects 3-43, wherein the contacting step comprises contacting 1) the transition metal precursor compound comprising at least one first ligand with 2) the at least one second ligand to form a pre-contacted mixture, followed by contacting the pre-contacted mixture with the remaining components 3)-6) in any order to provide the reaction mixture.

Aspect 47. The process according to any one of aspects 1-2 or 4-43, wherein the contacting step comprises contacting the metalalactone, the diluent, and the metal-treated chemically-modified solid oxide in any order.

Aspect 48. The process according to any one of aspects 1-47, wherein the reaction conditions suitable to form the α,β-unsaturated carboxylic acid or the salt thereof comprise contacting the reaction mixture with any suitable acid, or any acid disclosed herein, e.g., HCl, acetic acid, etc.

Aspect 49. The process according to any one of aspects 1-48, wherein the reaction conditions suitable to form the α,β-unsaturated carboxylic acid or the salt thereof comprise contacting the reaction mixture with any suitable solvent, or any solvent disclosed herein, e.g., carbonyl-containing solvents such as ketones, esters, amides, etc. (e.g., acetone, ethyl acetate, N,N-dimethylformamide), alcohols, water, etc.

Aspect 50. The process according to any one of aspects 1-49, wherein the reaction conditions suitable to form the α,β-unsaturated carboxylic acid or the salt thereof comprise heating the reaction mixture to any suitable temperature, or a temperature in any range disclosed herein, e.g., from 50° C. to 1000° C., from 100° C. to 800° C., from 150° C. to 600° C., from 250° C. to 550° C., etc.

Aspect 51. The process according to any one of aspects 1-50, wherein the molar yield of the α,β-unsaturated carboxylic acid, or the salt thereof, based on the metalalactone (in those preceding aspects comprising a metalalactone) or based on the transition metal precursor compound (in those preceding aspects comprising a transition metal precursor compound) is in any range disclosed herein, e.g., at least 20%, at least 40%, at least 60%, at least 80%, at least 100%, at least 120%, at least 140%, at least 160%, at least 180%, at least 200%, at least 250%, at least 300%, at least 350%, at least 400%, at least 450%, at least 500%, at least 750%, at least 1,000%, at least 1,250%, or at least 1,500%, etc.

Aspect 52. The process according to any one of aspects 1-51, wherein the contacting step and/or the subjecting step is/are conducted at any suitable pressure or at any pressure disclosed herein, e.g., from 5 psig (34 KPa) to 10,000 psig (68,948 KPa), from 45 psig (310 KPa) to 1000 psig (6,895 KPa), etc.

Aspect 53. The process according to any one of aspects 1-52, wherein the contacting step and/or the subjecting step is/are conducted at any suitable temperature or at any temperature disclosed herein, e.g., from 0° C. to 250° C., from 0° C. to 95° C., from 15° C. to 70° C., etc.

Aspect 54. The process according to any one of the aspects 1-53, wherein the contacting step and/or the subjecting step is conducted at any suitable weight hourly space velocity (WHSV) or any WHSV disclosed herein, e.g., from 0.05 to 50 hr$^{-1}$, from 1 to 25 hr$^{-11}$, from 1 to 5 hr$^{-1}$, etc., based on the amount of the metal-treated chemically-modified solid oxide.

Aspect 55. The process according to any one of aspects 1-54, wherein the process further comprises a step of isolating the α,β-unsaturated carboxylic acid, or the salt thereof, e.g., using any suitable separation/purification procedure or any separation/purification procedure disclosed herein, e.g., evaporation, distillation, chromatography, etc.

Aspect 56. The process according to any one of aspects 1-55, wherein the metal-treated chemically-modified solid oxide is arranged as a fixed bed, a bubbling bed, a moving bed, or a stirred bed.

Aspect 57. The process according to any one of aspects 1-56, wherein the α,β-unsaturated carboxylic acid or the salt thereof comprises any suitable α,β-unsaturated carboxylic acid, or any α,β-unsaturated carboxylic acid disclosed herein, or the salt thereof, e.g., acrylic acid, methacrylic acid, 2-ethylacrylic acid, cinnamic acid, sodium acrylate, potassium acrylate, magnesium acrylate, sodium (meth) acrylate, etc.

Aspect 58. The process according to any one of aspects 3-57, wherein the olefin comprises any suitable olefin or any olefin disclosed herein, e.g. ethylene, propylene, butene (e.g., 1-butene), pentene, hexene (e.g., 1-hexene), heptane, octene (e.g., 1-octene), styrene, etc.

Aspect 59. The process according to any one of aspects 3-58, wherein the olefin is ethylene, and the step of contacting the transition metal precursor compound with the olefin and carbon dioxide ($CO_2$) is conducted using any suitable pressure of ethylene, or any pressure of ethylene disclosed herein, e.g., from 10 psig (69 KPa) to 1,000 psig (6895 KPa), from 25 psig (172 KPa) to 500 psig (3,447 KPa), or from 50 psig (345 KPa) to 300 psig (2,068 KPa), etc.

Aspect 60. The process according to any one of aspects 3-59, wherein the olefin is ethylene, and the step of contacting a transition metal precursor compound with the olefin and carbon dioxide ($CO_2$) is conducted using a constant addition of the olefin and carbon dioxide to provide the reaction mixture.

Aspect 61. The process according to any one of aspects 3-60, wherein the ethylene and carbon dioxide ($CO_2$) are constantly added in an ethylene:$CO_2$ molar ratio of from 3:1 to 1:3, to provide the reaction mixture.

Aspect 62. The process according to any one of aspects 3-61, wherein the step of contacting a transition metal precursor compound with the olefin and carbon dioxide ($CO_2$) is conducted using any suitable pressure of $CO_2$, or any pressure of $CO_2$ disclosed herein, e.g., from 20 psig (138 KPa) to 2,000 psig (13,790 KPa), from 50 psig (345 KPa) to 750 psig (5,171 KPa), or from 100 psig (689 KPa) to 300 psig (2,068 KPa), etc.

Aspect 63. The process according to any one of aspects 1-62, further comprising a step of monitoring the concentration of at least one reaction mixture component, at least one elimination reaction product, or a combination thereof.

Aspect 64. The process according to any one of aspects 1-63, wherein the metal of the metalalactone or the metal of the transition metal precursor compound is a Group 8-11 transition metal.

Aspect 65. The process according to any one of aspects 1-63, wherein the metal of the metalalactone or the metal of the transition metal precursor compound is Cr, Fe, Co, Ni, Cu, Mo, Ru, Rh, Pd, W, Ag, Ir, Pt, or Au.

Aspect 66. The process according to any one of aspects 1-63, wherein the metal of the metalalactone or the metal of the transition metal precursor compound is Ni, Fe, or Rh.

Aspect 67. The process according to any one of aspects 1-63, wherein the metal of the metalalactone or the metal of the transition metal precursor compound is Ni.

Aspect 68. The process according to any one of aspects 1-63, wherein the metalalactone is a nickelalactone, e.g., any suitable nickelalactone or any nickelalactone disclosed herein, or wherein the metal of the transition metal precursor compound is Ni.

Aspect 69. The process according to any one of aspects 1-68, wherein any of the metalalactone compound, the first ligand, or the second ligand comprises any suitable neutral electron donor group and/or Lewis base, or any neutral electron donor group and/or Lewis base disclosed herein.

Aspect 70. The process according to any one of aspects 1-68, wherein any of the metalalactone compound, the first ligand, or the second ligand comprises a bidentate ligand.

Aspect 71. The process according to any one of aspects 1-68, wherein any of the metalalactone compound, the first ligand, or the second ligand comprises at least one of a nitrogen, phosphorus, sulfur, or oxygen heteroatom.

Aspect 72. The process according to any one of aspects 1-68, wherein any of the metalalactone compound, the first ligand, or the second ligand comprises or is selected from a diphosphine ligand, a diamine ligand, a diene ligand, a diether ligand, or dithioether ligand.

Aspect 73. The process according to any one of aspects 1-68, wherein any of the metalalactone compound, the first ligand, or the second ligand comprises or is selected from a) an asymmetric ligand (comprising different donor atoms) such as 2-pyridylphosphine or b) an N-heterocyclic carbene (NHC) ligand.

Aspect 74. The process according to any one of aspects 1-73, wherein the metalalactone compound, the transition metal precursor compound, the first ligand, the second ligand, the olefin, the diluent, the chemically-modified solid oxide, the metal-treated chemically-modified solid oxide, the sulfur oxoacid anion-modified solid oxide, the phosphorus oxoacid anion-modified solid oxide, the halide ion-modified solid oxide, the sulfur oxoacid or the salt thereof, the phosphorus oxoacid or the salt thereof, the hydrohalic acid or the halide salt, the metal cation, the acid used in combination with the metal cation, and the reaction conditions, are [a] any suitable, or [b] any disclosed metalalactone compound, transition metal precursor compound, first ligand, second ligand, olefin, diluent, chemically-modified solid oxide, metal-treated chemically-modified solid oxide, sulfur oxoacid anion-modified solid oxide, phosphorus oxoacid anion-modified solid oxide, sulfur oxoacid or salt thereof, phosphorus oxoacid or salt thereof, metal cation, acid used in combination with the metal cation, and reaction conditions.

Aspect 75. A process for forming an α,β-unsaturated carboxylic acid or a salt thereof, the process comprising:
a) contacting
i) a metalalactone compound comprising a Group 8-10 metal;
ii) a diluent; and
iii) a sulfur oxoacid anion-modified solid oxide or a halide ion-modified solid oxide that has been treated with [1] a sodium base, or [2] a sodium salt and an acid, to provide a reaction mixture; and
b) subjecting the reaction mixture to reaction conditions suitable to induce a metalalactone elimination reaction to form the α,β-unsaturated carboxylic acid or the salt thereof.

Aspect 76. A process for forming an α,β-unsaturated carboxylic acid or a salt thereof, the process comprising:
a) contacting in any order
i) a group 8-11 transition metal precursor;
ii) an olefin;
iii) carbon dioxide ($CO_2$);
iv) a diluent; and
v) a sulfur oxoacid anion-modified solid oxide or a halide ion-modified solid oxide that has been treated with [1] a sodium base, or [2] a sodium salt and an acid, to provide a reaction mixture; and
b) subjecting the reaction mixture to reaction conditions suitable to produce the α,β-unsaturated carboxylic acid or the salt thereof.

Aspect 77. A process for forming an α,β-unsaturated carboxylic acid or a salt thereof, the process comprising:
a) contacting in any order
i) a group 8-11 transition metal catalyst;
ii) an olefin;
iii) carbon dioxide ($CO_2$);
iv) a diluent; and
v) a sulfur oxoacid anion-modified solid oxide, a phosphorus oxoacid anion-modified solid oxide, or a halide ion-modified solid oxide that has been treated with [1] a sodium base, or [2] a sodium salt and an acid, to provide a reaction mixture; and
b) contacting the reaction mixture with [1] an alkali metal-containing base selected from an alkali metal or an alkaline earth metal oxide, hydroxide, alkoxide, aryloxide, amide, alkyl amide, arylamide, or carbonate, or [2] an alkali metal salt and an acid to produce an α,β-unsaturated carboxylic acid salt;
wherein the contacting step is carried out in the absence of a non-nucleophilic base.

We claim:

1. A process for forming an α,β-unsaturated carboxylic acid or a salt thereof, the process comprising:
a) contacting in any order
i) a transition metal precursor compound comprising at least one first ligand;
ii) optionally, at least one second ligand;
iii) an olefin;
iv) carbon dioxide ($CO_2$);
v) a diluent; and
vi) a metal-treated chemically-modified solid oxide to provide a reaction mixture, wherein the chemically-modified solid oxide comprises a sulfur oxoacid anion-modified solid oxide, a phosphorus oxoacid anion-modified solid oxide, or a halide ion-modified solid oxide; and
b) subjecting the reaction mixture to reaction conditions suitable to form the α,β-unsaturated carboxylic acid or the salt thereof;
wherein the transition metal precursor compound is present in the reaction mixture at a concentration of less than 0.1 mM (millimolar).

2. The process according to claim 1, wherein the transition metal precursor compound is present in the reaction mixture at a concentration of from 0.02 mM to 0.001 mM.

3. The process according to claim 1, wherein the metal-treated chemically-modified solid oxide is prepared by [a] contacting a solid oxide with a sulfur oxoacid anion, a phosphorus oxoacid anion, or a halide ion to provide the chemically-modified solid oxide, followed by [b] contacting the chemically-modified solid oxide with [1] a metal-containing base or [2] a metal-containing salt in combination with an acid.

4. The process according to claim 1, wherein the solid oxide of the chemically-modified solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof.

5. The process according to claim 1, wherein the chemically-modified solid oxide comprises a solid oxide that is chemically modified with an electron-withdrawing anion, the electron-withdrawing anion comprising sulfate, bisulfate, fluoro sulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof.

6. The process according to claim 1, wherein the metal-treated chemically-modified solid oxide comprises metal cations selected from a Group 1, 2, 12 or 13 metal.

7. The process according to claim 1, wherein the metal-treated chemically-modified solid oxide is selected from sodium-treated sulfated alumina, sodium-treated fluorided silica-coated alumina, sodium-treated fluorided silica-alumina, potassium-treated sulfated alumina, potassium-treated fluorided silica-coated alumina, potassium-treated fluorided silica-alumina, or any combination thereof.

8. The process according to claim 1, wherein the diluent comprises an ether diluent, a carbonyl-containing diluent, an aromatic hydrocarbon diluent, a halogenated aromatic hydrocarbon diluent, or an alcohol diluent.

9. The process according to claim 1, wherein the diluent comprises carbon dioxide, or wherein at least a portion of the diluent comprises the α,β-unsaturated carboxylic acid or the salt thereof, formed in the process.

10. The process according to claim 1, wherein the contacting step and/or the subjecting step is/are conducted at a pressure from 45 psig (310 KPa) to 1000 psig (6,895 KPa).

11. The process according to claim 1, wherein the contacting step and/or the subjecting step is/are conducted at a temperature from 0° C. to 95° C.

12. The process according to claim 1, wherein the contacting step and/or the subjecting step is/are conducted at a weight hourly space velocity (WHSV) of from 0.05 to 50 $hr^{-1}$, based on the amount of the metal-treated chemically-modified solid oxide.

13. The process according to claim 1, wherein the olefin is ethylene, and the step of contacting a transition metal precursor compound with the olefin and carbon dioxide ($CO_2$) is conducted an ethylene pressure of from 10 psig (69 KPa) to 1,000 psig (6895 KPa) and a $CO_2$ pressure of from 20 psig (138 KPa) to 2,000 psig.

14. The process according to claim 1, wherein the olefin comprises ethylene, propylene, butene, pentene, hexene, heptane, octene, or styrene.

15. The process according to claim 1, wherein the process further comprises a step of isolating the α,β-unsaturated carboxylic acid or the salt thereof.

16. The process according to claim 1, wherein the metal-treated chemically-modified solid oxide is arranged as a fixed bed, a bubbling bed, a moving bed, or a stirred bed.

17. The process according to claim 1, wherein the α,β-unsaturated carboxylic acid or the salt thereof is acrylic acid, methacrylic acid, or a salt thereof.

18. The process according to claim 1, wherein the transition metal of the transition metal precursor compound is Cr, Fe, Co, Ni, Cu, Mo, Ru, Rh, Pd, W, Ag, Ir, Pt, or Au.

19. The process according to claim 1, wherein the transition metal of the transition metal precursor compound is a Group 8-11 transition metal.

20. The process according to claim 1, further comprising a step of:
   c) regenerating the metal-treated chemically-modified solid oxide, comprising contacting the metal-treated chemically-modified solid oxide remaining following step b with [1] a metal-containing base or [2] a metal-containing salt in combination with an acid.

21. A process for forming an α,β-unsaturated carboxylic acid or a salt thereof according to claim 1, wherein
   the reaction mixture comprises a metalalactone compound, and
   wherein the metalalactone is present in the reaction mixture at a concentration of less than 0.2 mM (millimolar).

22. The process according to claim 21, wherein the metalalactone compound is present in the reaction mixture at a concentration of from 0.02 mM to 0.001 mM.

23. The process according to claim 21, wherein the metal-treated chemically-modified solid oxide is prepared by [a] contacting a solid oxide with a sulfur oxoacid anion, a phosphorus oxoacid anion, or a halide ion to provide the chemically-modified solid oxide, followed by [b] contacting the chemically-modified solid oxide with [1] a metal-containing base or [2] a metal-containing salt in combination with an acid.

24. The process according to claim 21, wherein:
   the solid oxide of the chemically-modified solid oxide comprises silica, alumina, titania, zirconia, magnesia, boria, calcia, zinc oxide, silica-alumina, silica-coated alumina, silica-titania, silica-zirconia, silica-magnesia, alumina-titania, alumina-zirconia, zinc-aluminate, alumina-boria, silica-boria, aluminum phosphate, aluminophosphate, aluminophosphate-silica, magnesium aluminate, titania-zirconia, or any combination thereof;
   the chemically-modified solid oxide comprises a solid oxide that is chemically modified with an electron-withdrawing anion, the electron-withdrawing anion comprising sulfate, bisulfate, fluorosulfate, phosphate, fluorophosphate, triflate, mesylate, tosylate, thiosulfate, $C_1$-$C_{10}$ alkyl sulfonate, $C_6$-$C_{14}$ aryl sulfonate, fluoride, chloride, or any combination thereof; and
   the metal of the metal-treated chemically-modified solid oxide comprises metal cations selected from a Group 1, 2, 12 or 13 metal.

25. The process according to claim 21, wherein the contacting step and/or the subjecting step is/are conducted at a pressure from 45 psig (310 KPa) to 1000 psig (6,895 KPa), a temperature from 0° C. to 95° C., and a weight hourly space velocity (WHSV) of from 0.05 to 50 hr$^{-1}$, based on the amount of the metal-treated chemically-modified solid oxide.

26. The process according to claim 21, wherein the metalalactone compound comprises a Group 8-11 transition metal.

27. The process according to claim 21, further comprising a step of:
   c) regenerating the metal-treated chemically-modified solid oxide, comprising contacting the metal-treated chemically-modified solid oxide remaining following step b with [1] a metal-containing base or [2] a metal-containing salt in combination with an acid.

28. A process for forming an α,β-unsaturated carboxylic acid or a salt thereof according to claim 1, wherein
   the transition metal compound is a group 8-11 transition metal catalyst;
   the metal-treated chemically-modified solid oxide comprises a sulfur oxoacid anion-modified solid oxide, a phosphorus oxoacid anion-modified solid oxide, or a halide ion-modified solid oxide that has been treated with [1] a sodium base, or [2] a sodium salt and an acid, to provide a reaction mixture; and
   the reaction conditions suitable to form the α,β-unsaturated carboxylic acid or the salt thereof comprise contacting the reaction mixture with [1] an alkali metal-containing base selected from an alkali metal or an alkaline earth metal oxide, hydroxide, alkoxide, aryloxide, amide, alkyl amide, arylamide, or carbonate, or [2] an alkali metal salt and an acid selected from sulfuric acid, fluoro sulfuric acid, phosphoric acid, fluorophosphoric acid, triflic (trifluoromethanesulfonic) acid, a $C_1$-$C_{10}$ alkyl sulfonic acid, or a $C_6$-$C_{14}$ aryl sulfonic acid to produce an α,β-unsaturated carboxylic acid salt.

29. The process according to claim 1, wherein the transition metal precursor compound is present in the reaction mixture at a concentration of less than 0.05 mM.

30. The process according to claim 1, wherein the transition metal precursor compound is present in the reaction mixture at a concentration of more than about 0.0001 mN.

31. The process according to claim 21, wherein the reaction mixture comprises an adduct of the metalalactone and the metal-treated chemically-modified solid oxide.

* * * * *